United States Patent [19]

Bundy

[11] 3,950,363

[45] Apr. 13, 1976

[54] PROSTAGLANDIN CYCLIC ETHERS
[75] Inventor: Gordon L. Bundy, Kalamazoo, Mich.
[73] Assignee: The Upjohn Company, Kalamazoo, Mich.
[22] Filed: Mar. 10, 1975
[21] Appl. No.: 556,768

[52] U.S. Cl. ...... 260/347.3; 260/347.5; 260/468 D; 260/483; 260/484 R; 260/514 D; 424/285
[51] Int. Cl.² .................................. C07D 307/00
[58] Field of Search ........... 260/347.3, 347.4, 347.5

[56] References Cited
UNITED STATES PATENTS
3,879,438  4/1975  Crabbe et al. .................. 260/347.3

Primary Examiner—Henry R. Jiles
Assistant Examiner—Bernard I. Dentz
Attorney, Agent, or Firm—Earl C. Spaeth

[57] ABSTRACT

The disclosure includes novel cyclic ethers of the formulas:

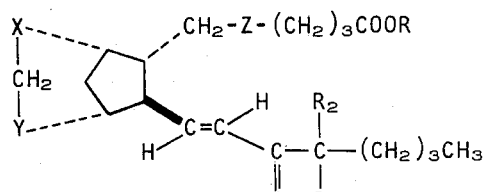

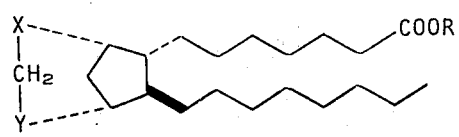

in these formulas, X and Y are —O— or a valence bond with the proviso that one of X and Y is —O— and the other is a valence bond; R is hydrogen, alkyl of one to 4 carbon atoms, inclusive, or a pharmacologically acceptable cation; $R_2$ and $R_3$ are hydrogen, methyl, or ethyl; and A is $R_4\overset{\frown}{O}H$ or $R_4\overset{\frown}{O}H$ wherein $R_4$ is hydrogen, methyl, or ethyl with the proviso that $R_2$ and $R_3$ are both hydrogen when $R_4$ is methyl or ethyl. The compounds of the first of these formulas are useful as vasoconstrictors and enhancers of platelet aggregation, and are useful in the control of bleeding in mammals, including man. The compounds of the second of these formulas are useful in the treatment of inflammation.

25 Claims, No Drawings

PROSTAGLANDIN CYCLIC ETHERS

DESCRIPTION OF THE INVENTION

This invention relates to novel compositions of matter, and to novel processes and novel intermediates useful in making these compounds. More specifically, this invention is concerned with novel cyclic ethers of the formula:

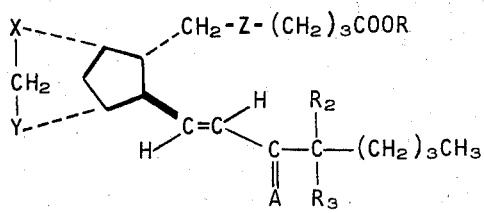

wherein X and Y are —O— or a valence bond with the proviso that one of X and Y is —O— and the other is a valence bond; wherein Z is —$CH_2CH_2$— or cis-CH=CH—, wherein R is hydrogen, alkyl of one to 4 carbon atoms, inclusive, or a pharmacologically acceptable cation; wherein $R_2$ and $R_3$ are hydrogen, methyl, or ethyl; and wherein A is

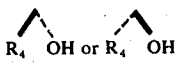

wherein $R_4$ is hydrogen, methyl, or ethyl with the proviso that $R_2$ and $R_3$ are both hydrogen when $R_4$ is methyl or ethyl. Included within the scope of formula I are compounds of the formulas:

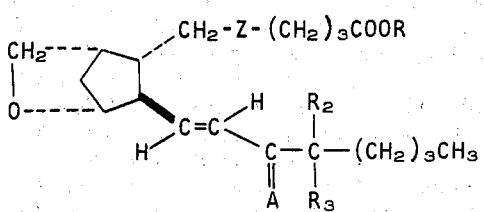

and

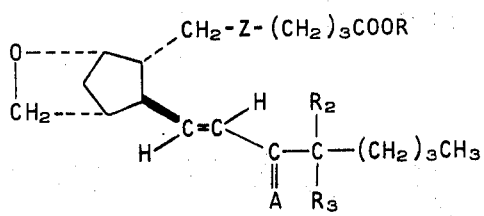

wherein Z, R, $R_2$, $R_3$, and A are as defined above.

This invention is also specifically concerned with novel cyclic ethers of the formula:

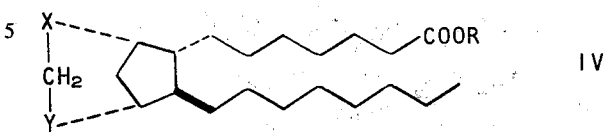

wherein X and Y are —O— or a valence bond with the proviso that one of X and Y is —O— and the other is a valence bond, and wherein R is hydrogen, alkyl of one to 4 carbon atoms, inclusive, or a pharmacologically acceptable cation. Included within the scope of formula IV are compounds of the formulas:

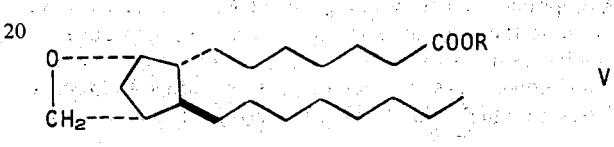

and

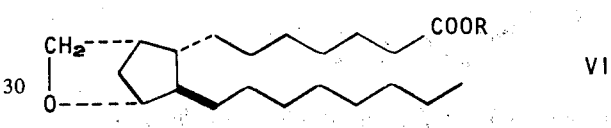

wherein R is as defined above.

This invention is also specifically concerned with novel methods for making these novel compounds of formulas I, II, III, IV, V, and VI, and with novel chemical intermediates useful in those methods.

The novel compounds of formulas I, II, III, IV, V, and VI are related in structure to the substance known as prostanoic acid which has the formula and atom numbering:

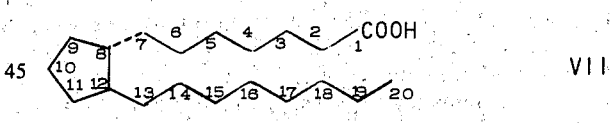

There are various derivatives and derivative-analogs of prostanoic acid already known in the art. These are known as prostaglandins and prostaglandin analogs. For example, the compound known as prostaglandin $E_1$ ($PGE_1$) has the formula:

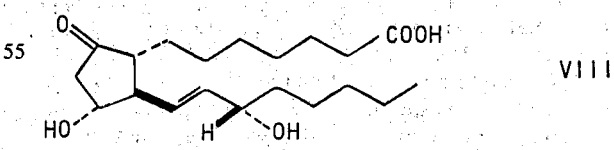

The compound known as prostaglandin $E_2$ ($PGE_2$) has the formula:

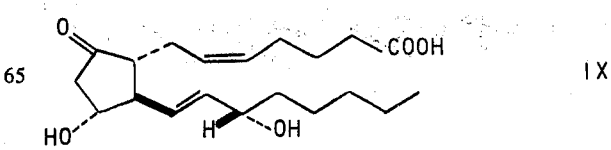

The compound known as prostaglandin $F_{1\alpha}$ (PGF$_{1\alpha}$) has the formula:

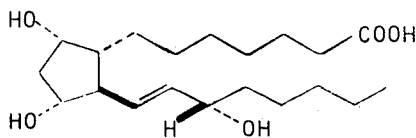

X

The compound known as prostaglandin $F_2$ (PGF$_2$) has the formula:

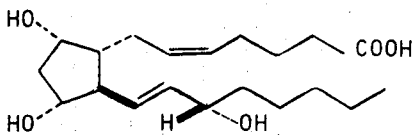

XI

Compounds corresponding to PGE$_1$ and PGE$_2$ but without the ring hydroxy and with a carbon-carbon double bond between C-10 and C-11 in the ring are also known. These are named prostaglandins A (PGA). Thus, prostaglandin A$_1$ (PGA$_1$) has the formula:

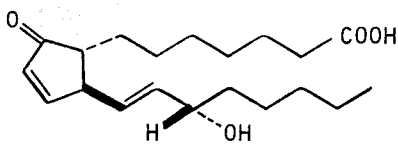

XII

Prostaglandin A$_2$ (PGA$_2$) has the formula:

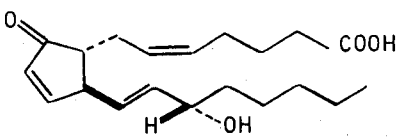

XIII

Prostaglandin-like compounds corresponding to formulas VII–XIII but with a methyl or ethyl group in place of the hydrogen at C-15, or with one or two methyl or ethyl groups in place of one or two of the hydrogens at C-16 are also known in the art. See, for example, U.S. Pat. Nos. 3,728,382 and 3,813,433, and German Offlenlegungsschrift 2,145,600. Also known in the art are compounds corresponding to formulas VII–XIII and the above-mentioned alkyl substituted compounds but with the opposite stereochemical configuration at C-15.

Prostaglandin-like compounds corresponding to formulas VII and VIII but with the two ring hydroxy groups joined to form an endoperoxide grouping are also known in the art. See, for example, Hamberg et al., Proc. Nat. Acad. Sci. USA 70 (3), 899 (1973), Hamberg et al., Proc. Nat. Acad. Sci. USA 71 (2), 345 (1974), Nugteren et al., Biochim. Biophys. Acta 326, 448 (1973). An example of this type of endoperoxide is the compound known as PGH$_2$, with the structure:

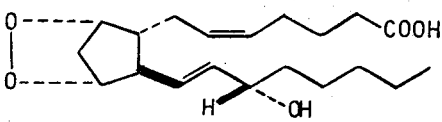

XIV

See also Wlodawer et al., J. Am. Chem. Soc. 93, 2815 (1971).

Molecules of the compounds encompassed by formulaS I to XIV above each have several centers of asymmetry. These formulas, including formulas I, II, III, IV, V, and VI which represent the novel cyclic ethers of this invention, are intended to represent optically active compounds each with the same absolute configuration as optically active prostaglandin E$_1$ (PGE$_1$) obtained from certain mammalian tissues, for example, sheep vesicular glands or human seminal plasma. See, for example, Bergström et al., J. Biol. Chem. 238, 3555 (1963), Horton, Experientia, 21, 113 (1965), Bergstrom et al. Pharmacol. Rev. 20, 1 (1968), and references cited in those.

In formulas I to XIV, a broken line attachment to the cyclopentane ring indicates a chain in alpha configuration, i.e., below the plane of the cyclopentane ring. A heavy solid line attachment to the cyclopentane ring indicates a chain in beta configuration, i.e., above the plane of the cyclopentane ring. The configuration for the side chain hydroxy shown in formulas VIII–XIII is sometimes called S although alpha ($\alpha$) is preferred as a designation for this configuration. It should be noted that the novel cyclic ethers of formulas I, II, and III include not only this S or alpha configuration for the C-15 hydroxy but also the opposite configuration at C-15 which is designated variously as epi, R, and beta ($\beta$), the last being the preferred designation. See Nature, 212, 38 (1966), and Nelson, J. Med. Chem. 17, 911 (1974) for discussions of prostaglandin absolute configuration and nomenclature.

Although formulas I, II, III, IV, V, and VI as written herein define only optically active compounds corresponding in absolute configuration to that of natural PGE$_1$, it is intended that these formulas as written hereinabove and in the various claims hereinafter include within their scope also the corresponding racemic compounds but not the optically active compounds which are defined by the mirror image of those formulas.

It is useful in naming the novel cyclic ethers of formulas I–VI and also the chemical intermediates used as described hereinafter, to base the names on one of the known prostaglandins of formulas VIII, IX, X, and XI, namely PGE$_1$, PGE$_2$, PGF$_{1\alpha}$, and PGF$_{2\alpha}$, respectively, or to base the names on the compound of formula VII, namely prostanoic acid, using in both cases, the carbon atom numbering shown in formula VII. For the cyclic ethers in particular, the designation "epoxymethano" will mean the atom grouping —O—CH$_2$—. Thus, the compound of formula II wherein Z is cis-CH=CH—, A is

and R$_1$, R$_2$, and R$_3$ are hydrogen will have the name 9,11-dideoxy-11$\alpha$,9$\alpha$-epoxymethano-PGF$_{2\alpha}$, showing relative to PGF$_{2\alpha}$ (formula XI), that this compound lacks the oxygens attached to positions 9 and 11. This name also shows the presence of the epoxymethano moiety, with the oxygen end attached in alpha configuration to position 11 and the CH$_2$ end attached in alpha configuration to position 9. Similarly, the compound of formula III wherein Z is —CH$_2$CH$_2$—, A is

and $R_1$, $R_2$, and $R_3$ will have the name 9,11-dideoxy-9α,11α-epoxymethano-15β-PGF$_{1\alpha}$, showing relative to PGF$_{1\alpha}$ (formula X), that this compound also lacks the oxygens attached to positions 9 and 11. This name also shows the presence of the epoxymethano moiety, with the oxygen end attached in alpha configuration to position 9 and the CH$_2$ end attached in alpha configuration to position 11. The name also shows the R or beta configuration for the hydroxy at C-15 rather than the S or alpha configuration as in PGF$_{1\alpha}$. Similarly, the compound of formula V wherein R is hydrogen will have the name 9α,11α-(epoxymethano)prostanoic acid, showing the presence of the epoxymethano moiety, with th oxygen end attached in alpha configuration to position 9 and the CH$_2$ end attached in alpha configuration to position 11. The cyclic ethers of formula VI are named in like manner, namely as 11α,9α-(epoxymethano)prostanoic acid and its salts and alkyl esters. Also the various intermediates mentioned hereinafter are named in a similar manner as variations of PGE$_1$, PGE$_2$, PGF$_{1\alpha}$, and PGF$_{2\alpha}$.

The novel formula I, II, and III cyclic ethers of this invention cause vascular constriction in laboratory animals and induce the aggregation of blood platelets, both at low concentrations. Accordingly, these novel compounds are useful in the control of bleeding in mammals, including man, useful large domestic animals including cattle and horses, and smaller domestic animals, including dogs and cats, where vascular constriction is desired and where enhanced local platelet aggregation is also advantageous. A preferred route of administration for this purpose is a local application of the compound to the bleeding site, especially topically, when rapid cessation of bleeding is desired, for example, during or after dental or other oral surgery or after nasal surgery. Topical application is readily achieved by administering the compound to the bleeding site in an appropriate carrier. The carrier is either inert with respect to hemostasis, or when desired, the carrier itself has hemostatic activity. Examples of compositions wherein the carrier is non-hemostatic are aqueous solutions with or without the usual additives to provide isotonic or buffered solutions, and with or without other diluents, for example, ethanol. Alternatively, non-aqueous solutions, such as a glycerol solution, or other aqueous or non-aqueous preparations, for example, ointments, suppositories, and aerosol packs are used for topical and body cavity treatment. An example of compositions wherein the carrier itself is hemostatic involves incorporation of the compound in an absorbable gelatin sponge, for example, sponges sold under the name Gelfoam.

Solutions of these compounds intended for topical use are preferably in the concentration range 0.1 μg. to 100 μg. per ml., more preferably in the range 1 μg. to 20 μg. per ml. Hemostatic surgical sponges preferably contain 0.2 to 2000 μg. per gram of sponge, more preferably 1 μg. to 50 μg. per gram of sponge. Such sponges are used to control bleeding in various types of surgery including dental, oral, nasal, gastric-duodenal, rectal, prostatic, gynecological, neurological, and general surgery, and also bleeding resulting from other causes, for example, injury.

The novel formula I, II, and III compounds also have bronchoconstrictor activity, and for this reason, care is to be exercised in administration of the compounds to control bleeding. Ordinarily, single doses to a bleeding site should not exceed 10 μg. per kg. of body weight, and should not be repeated more often than necessary to reduce bleeding. Repeated doses should be interrupted if signs of bronchoconstriction are observed. Patients should also be monitored for signs of excessive increase of blood pressure, decrease of heart rate, and onset of chest pain during administration of these compounds, and administration of the compound should be suspended until normal base lines in these regards are restored.

These novel compounds I, II, and III are also administered systemically, for example, by intravenous infusion, to control internal bleeding, for example, internal injuries or gastrointestinal bleeding from ulcers. For this purpose, sterile aqueous solutions of the composition and concentration range mentioned above for topical application are used. Here also, care is to be taken to watch for the side effects of bronchoconstriction, increase in blood pressure, decrease of heart rate, and onset of chest pain, and to interrupt the infusion or reduce the infusion rate until such side effects are under control.

The novel formula I, II, and III compounds of this invention are unusually stable in aqueous solution compared with other known prostaglandin-like compounds with similar biological properties. Therefore, these novel compounds are also useful as standards in in vitro and in vivo test systems to produce standardized bronchoconstrictive, vasoconstrictive, and platelet aggregative responses. Systems using these novel compounds are thus useful in assaying the potency and efficacy of other bronchodilators, vasodilators, and inhibitors of platelet aggregation, and in screening other compounds for such activities.

The novel formula IV, V, and VI cyclic ethers of this invention are highly active as inhibitors of the prostaglandin synthetase enzyme system. Regarding prostaglandin synthetase inhibition, see, for example, Vane, Nature New Biology, 231, 232 (1971), Takeguchi et al., Prostaglandins, 2, 169 (1972), and references cited in those. Accordingly, these novel compounds are useful for administration to mammals, including humans, whenever it is desirable medically to inhibit this enzyme system. For example, these novel compounds are useful as anti-inflammatory agents in mammals and especially humans, and for this purpose, are administered systemically and preferably orally. For oral administration, a dose range of 0.01 to 100 μg. per kg. of human body weight is used to give relief from pain associated with inflammatory disorders such as rheumatoid arthritis. They are also administered intravenously in aggravated cases of inflammation, preferably in a dose range 0.01 to 100 μg. per kg. per minute until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

For all of the above purposes, the novel formula I, II, III, IV, V, and VI cyclic ethers of this invention are used in free acid form, as esters, or in pharmacologically acceptable salt form.

When the ester form is used, any ester within the range of the above definition of R is used, i.e., alkyl of one to 4 carbon atoms, inclusive. These are methyl, ethyl, propyl, isopropyl, and each of the isomeric butyl groups. Of these, methyl and ethyl are especially preferred.

Pharmacologically acceptable salts of these novel cyclic ethers of formulas I, II, III, IV, V, and VI useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like, aliphatic, cycloaliphatic, and araliphatic amines containing up to and including about 18 carbon atoms, as well as heretocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

When one of the novel compounds of formulas I–VI is administered intravenously by injection or infusion for one of the above-described pharmacological purposes, it is preferred because of increased water solubility that R in the formula be hydrogen or a pharmacologically acceptable cation. For other routes of administration, any of the free acid form, salt form, or alkyl ester form of these novel compounds is used.

The novel cyclic ethers of formulas I, II, and III are prepared by the processes outlined in Charts I and II.

In Charts I and II, Z, $R_2$, $R_3$, and A are as defined above, $R_1$ is hydrogen or alkyl of one to 4 carbon atoms, inclusive, $R_5$ is a non-reactive organic radical as hereinafter further defined, and X is Br or Cl. It will be observed in Chart I and Chart II that formulas XIX and XXIII are the same as formulas II and III hereinabove except that R is used in formulas II and III in place of the $R_1$ in formulas XIX and XXIII of Charts I and II. The difference between R and $R_1$ is that R includes pharmacologically acceptable cations in addition to hydrogen and alkyl of one to 4 carbon atoms. The processes outlined in Charts I and II are not suitable for the preparation of the salts of these final products and, as will be discussed hereinafter, these salts (R in formulas II and III is a pharmacologically acceptable cation) are prepared from the corresponding free carboxylic acid forms of the formula XIX and XXIII compounds, namely wherein $R_1$ is hydrogen.

Turning now to Chart I, which shows the processes used to make products of formula III, the initial reactants of formula XV are known in the art. See, for example, U.S. Pat. Nos. 3,725,469, 3,759,965, 3,813,433, and German Offenlegungsschriften 2,217,044 and 2,145,600. These reactants of formula XV are all of the PGA-type. See, for example, illustrative formulas XII and XIII hereinabove.

CHART I

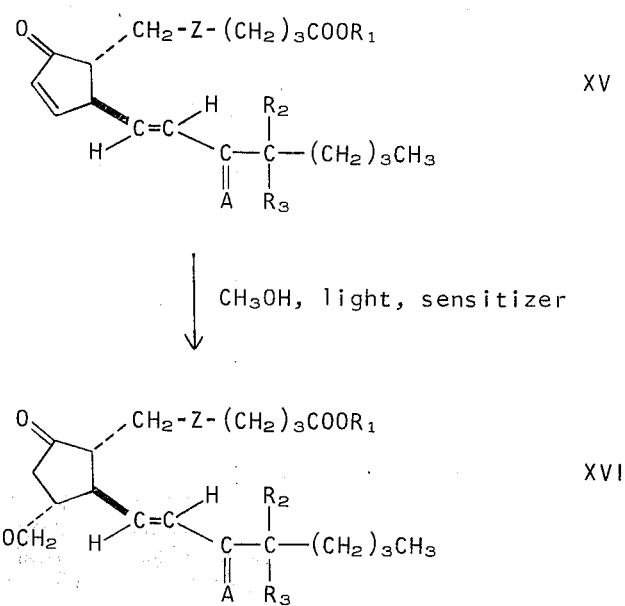

CHART I (Continued)
↓ carbonyl reducing agent
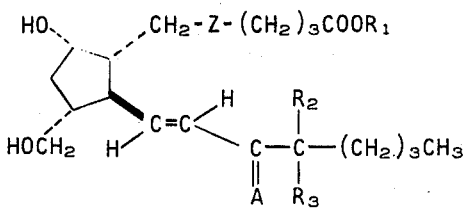  XVII
↓ $R_5SO_2X$
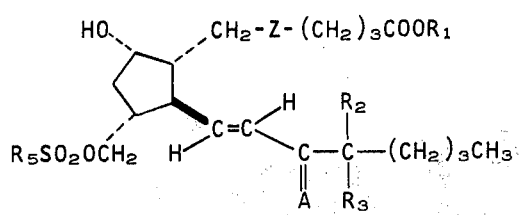  XVIII
↓ base
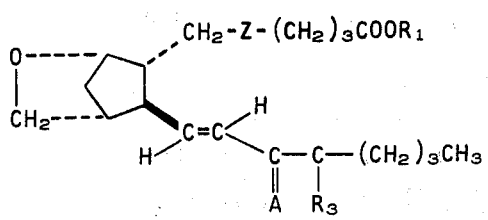  XIX
CHART II
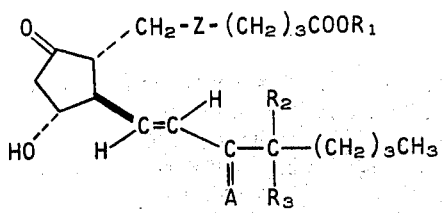  XX
↓ (1) silylation
(2) carbanion of an N-alkyl-S-methyl-S-arylsulfoximine
(3) Aluminum amalgam, water, acid CHART II (Continued)

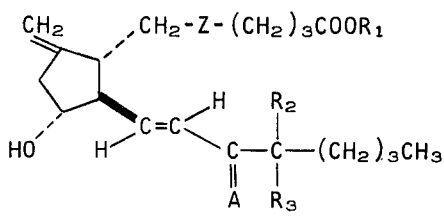

XXI (4) silylation (5) hydroboration-oxidation (6) $R_5SO_2X$ (7) hydrolysis of silyl groups

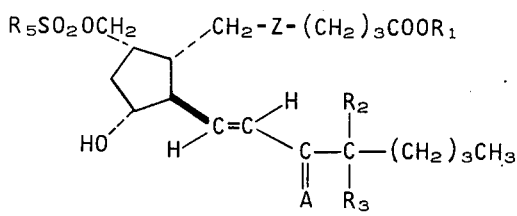

XXII base

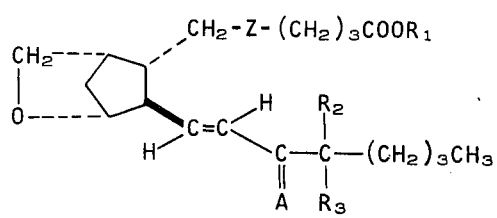

XXIII

The transformation of the initial PGA-type reactant of formula XV to the intermediate of formula XVI involves a photochemical addition of methanol to the endocyclic carbon-carbon double bond of the formula XV reactant. This reaction is carried out by methods known in the art for the 1,4-addition of alcohols to α,β-unsaturated carbonyl compounds. See, for example, Pfau et al., Compt. Rend. 254, 1817 (1962) and Fraser-Reid et al., J.C.S. Chem. Commun. 1286 (1972). For this reaction, light and a sensitizer are needed. Benzophenone is a suitable sensitizer, but other sensitizers as known in the art are also useful for this purpose. Light of 3500A is suitable for this reaction but other wavelengths, especially shorter wavelengths, are also useful for this purpose. It is preferred to use at least about one molecular amount of the sensitizer per molecular amount of the formula XV reactant. A mixture containing a major amount of the desired 11-alpha compound of formula XVI and a lesser amount of the corresponding 11-beta isomer is usually obtained, the 11-alpha compound being separated from the 11-beta isomer by methods known in the art, for example, by chromatography. The desired 11-alpha product is usually more polar than the 11-beta isomer. The 11-alpha isomer is also distinguished from the 11-beta isomer on the basis of optical rotatory dispersion and circular dichroism measurements. The 11-alpha isomer will have a more negative Cotton effect than the 11-beta isomer.

Referring again to Chart I, the novel intermediate of formula XVI is transformed to the further novel intermediate of formula XVII by reduction of the 9-oxo atom of XVI to the 9-hydroxy group of XVII. For this transformation, any reducing agent can be used which will reduce a ketonic carbonyl group to a secondary hydroxy without also reducing carbon-carbon double bonds or the carboxylate moiety. It should be noted, however, that the desired formula III intermediate has the 9-hydroxy in alpha configuration. Many of the known carbonyl reducing agents, for example, sodium borohydride, are relatively non-selective in producing hydroxy groups of both alpha and beta configuration when reducing a ring carbonyl group. Although these $9\alpha$ and $9\beta$ hydroxy compounds are usually separated easily by methods known in the art, for example, by chromatography, it is preferred to use for this XVI to XVII carbonyl reduction a reducing agent which results in formation of a major amount of the desired alpha isomer, and preferably a reducing agent which gives substantially complete reduction to the alpha isomer. One such preferred carbonyl reducing agent is lithium perhydro-9b-boraphenalylhydride. See, for example, Brown et al., J. Am. Chem. Soc. 92, 709 (1970). Procedures for using this particular reducing agent and other carbonyl reducing agents are known in the art.

Subsequent to my invention of the novel intermediates of formulas XVI and XVII wherein Z is cis-CH=CH—, A is

and $R_1$, $R_2$, and $R_3$ are hydrogen, those compounds were disclosed orally at the June 24–28, 1974, meeting of the Ninth International Symposium on the Chemistry of Natural Products in Ottawa, Canada, and at the August 5–9, 1974, Medicinal Chemistry Gordon Conference in New London, N.H.

Referring still again to Chart I, the novel intermediate of formula XVII is transformed to the corresponding sulfonic acid ester of formula XVIII wherein $R_5$ is a nonreactive organic radical. This is accomplished by the usual method for transforming hydroxy compounds to sulfonic acid esters, namely the reaction of the formula XVII intermediate with the corresponding sulfonyl chloride or bromide, $R_5SO_2X$, in the presence of a basic tertiary amine. Any sulfonyl chloride or bromide with a non-reactive $R_5$ moiety is useful in this reaction. By "non-reactive $R_5$ moiety" is meant a moiety such that no part of said moiety itself reacts with any portion of the formula XVII reactant, and such that no part of said moiety interferes with the subsequent transformation of the formula XVIII sulfonic acid ester to final product XIX. Especially preferred for this reaction are arylsulfonyl halides, especially the chlorides, wherein the aryl moiety is non-reactive itself and contains a single benzene ring directly attached to the sulfur of the $SO_2X$ moiety of $R_5SO_2X$ or a sulfonyl halide of similar reactivity toward primary hydroxyl groups. Especially preferred for this reaction is p-toluenesulfonyl chloride. By using a sulfonyl halide of such reactivity, undesired reaction with the 15-hydroxy of intermediate XVII is minimized. It is also preferred that no more than one molecular equivalent of the sulfonyl halide be used per molecular equivalent of the formula XVII intermediate.

Finally with regard to Chart I, the novel intermediate of formula XVIII is transformed to the cyclic ether product XIX by reaction of XVIII with a base. Useful bases for this purpose are alkali metal hydroxides, alkoxides, or hydrides, especially wherein the alkali metal is sodium or potassium. When it is desired that the formula XIX product be a free acid, i.e. $R_1$ is hydrogen, it is advantageous to use aqueous solutions of sodium or potassium hydroxides as bases, said solutions containing sufficient of a water miscible liquid diluent, e.g., methanol or ethanol, to give a homogenous reaction mixture. When XVIII is an ester, i.e., $R_1$ is alkyl of one to 4 carbon atoms, inclusive, and it is desired that XIX be the same ester, it is preferred to use a sodium or potassium alkoxide in an inert organic diluent, e.g., tetrahydrofuran, said alkoxide containing the same alkyl moiety as XVIII ($R_1$), or to use sodium or potassium tert-butoxide, also in an inert organic diluent. At least two molecular equivalents of the base per molecular equivalent of XVIII is used for this reaction. The reaction is advantageously carried out in the range about 10° to about 50° C., preferably at about 25° C., preferably in the absence of atmospheric oxygen. The formula XIX cyclic ether is isolated by procedures known in the art and exemplified hereinafter.

Referring again to the entire sequence of reactions set forth in Chart I, $R_1$ in the initial reactant is hydrogen or alkyl of one to 4 carbon atoms, inclusive. When a formula XIX product wherein $R_1$ is hydrogen is desired for one of the pharmacological purposes described hereinabove, it is preferred, however, that an initial formula XV reactant wherein $R_1$ is methyl or ethyl be used, and that the resulting final XIX product wherein $R_1$ is methyl or ethyl by saponified, preferably in the final reaction mixture, by known procedures to the formula XIX free acid ($R_1$ is hydrogen).

Turning now to Chart II, which shows the processes used to make products of formula II, the initial reactants of formula XX are known in the art. See, for example, U.S. Pat. Nos. 3,069,322, 3,598,858, 3,728,382, 3,813,433, and German Offenlegungsschrift 2,217,044. These reactants are all of the PGE-type. See, for example, illustrative formulas VIII and IX hereinabove.

As in the process sequence shown in Chart I leading from the formula XV reactant to the formula XIX cyclic ether product, $R_1$ in the Chart II process sequence is hydrogen or alkyl of one to 4 carbon atoms, inclusive. When a cyclic ether product of formula XXIII wherein $R_1$ is hydrogen is desired, it is, however, preferred, as in the Chart I process sequence, that a formula XX initial reactant wherein $R_1$ is methyl or ethyl be used, and the final cyclic ether product XXIII ($R_1$ is methyl or ethyl) then be saponified by known procedures to the formula XXIII free acid ($R_1$ is hydrogen).

The first step (1) in transformation of XX to XXI is the silylation of initial reactant XX. The intent of this reaction step is to replace in the formula XX reactant the hydrogens of the two hydroxy groups and the hydrogen of the carboxy group, if present, with protective groups which can be removed after a desired reaction which would otherwise cause an undesired change in said hydroxy groups or carboxy group or in which the hydrogens of the hydroxys or carboxy would otherwise interfere. For this purpose, any silyl diether or silyl diether-ester is used which will stay unchanged as a protective group as long as needed and then be easily removed by procedures which will not otherwise alter the desired molecule. The choice of appropriate protective silyl groups and procedures for forming them and removing them are within the skill of the art. Especially useful for the present purposes are silyl ethers and silyl ether-esters wherein the silyl moiety is of the formula —Si—(E)$_3$ wherein E is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive. The various E of an —Si—(E)$_3$ moiety are alike or different. For example, an —Si—(E)$_3$ can be trimethylsilyl, dimethylphenylsilyl, or methylphenylbenzylsilyl. An especially preferred silyl group for this purpose is trimethylsilyl.

These silyl diethers or diether-esters, including those of the —Si—(E)$_3$ type, are prepared by procedures known in the art using reagents known in the art or which can be prepared by methods known in the art. See, for example, Post, "Silicones and Other Organic Silicon Compounds," Reinhold Publishing Corp., New York, N.Y. (1949) and Pierce, "Silylation of Organic Compounds," Pierce Chemical Co., Rockford, Ill. (1968). Both hydroxy groups, C-11 and C-15, of the formula XX reactant are silylated, for example to —O—Si—(E)$_3$ moieties, and sufficient silylating agent is used according to known procedures to accomplish that. In the case of formula XX reactants wherein $R_1$ is hydrogen, excess silylating agent and a longer silylating reaction time is used to silylate the —COOH, for example to —COO—Si—(E)$_3$.

Referring again to Chart II, steps (2) and (3) in the transformation of XX to XXI involve the transformation of the 9-oxo atom of the silylated formula XX reactant to a 9-methylene (=CH$_2$) moiety. This transformation is accomplished by the procedure disclosed by Johnson et al., J. Am. Chem. Soc., 95, 6462 (1973), or by obvious modifications thereof.

The procedure of Johnson et al. involves the generation of a carbanion of an N-alkyl-derivative of an S-methyl-S-arylsulfoximine, for example, the carbanion of N,S-dimethyl-S-phenylsulfoximine (referred to by Johnson et al. as the N-methylphenylsulfonimidoylmethyl anion). This carbanion is generated by reacting the N-alkyl-S-methyl-S-arylsulfoximine with any of the usual reagents which will extract an active hydrogen from such sulfoximines, for example, an alkyllithium or an alkylmagnesium halide. Silylated formula XX reactant is mixed with the carbanion thus generated, and the resulting adduct is then mixed with aluminum amalgam in the presence of acetic acid and water to give the desired formula XXI 9-methylene intermediate.

For these steps (2) and (3) of this transformation of XX to XXI (Chart II), it appears to be important to use about three molecular equivalents of the N-alkyl-S-phenyl-S-methylsulfoximine per molecular equivalent of the silylated formula XX reactant. For reasons not fully understood, use of substantially more or less of the sulfoximine appears to result in lower yields of the desired formula XXI intermediate. One molecular equivalent of the hydrogen extracting reagent, e.g., methylmagnesium chloride or butyllithium is used for each equivalent of sulfoximine. The adduct formation is carried out in the range about 0° C. to about −100° C., preferably below about −50° C., advantageously at the temperature of solid carbon dioxide. An inert reaction diluent is used, preferably for ease of isolation of the adduct or when the adduct is not isolated prior to step (3), one which is miscible with water. Tetrahydrofuran is a suitable reaction diluent.

When the step (2) reaction is complete, the adduct is isolated by procedures known in the art or, alternatively the entire reaction mixture is used for step (3). When the adduct is isolated, it is advantageous to remove the protective silyl groups before proceeding with step (3) since that step does not require these protective groups. This removal of silyl groups is, however, not necessary, and a silylated adduct can be used for the step (3) reductive elimination. If it is desired, as is preferred, to remove silyl groups from the adduct, this is easily accomplished by treating the silylated adduct with an acid which does not alter the adduct other than by removal of silyl groups. Suitable acids for this purpose are dilute aqueous solutions of citric acid or phosphoric acid.

The reductive step (3) is carried out by contacting the adduct from step (2), with or without protective silyl groups, with aluminum amalgam, advantageously prepared as in Johnson et al., above cited, in the presence of aqueous acetic acid in the temperature range about 0° C. to about 50° C., preferably in the range about 20° to 30° C. Other carboxylic acids than acetic acid can also be used, for example, propionic acid, butyric acid, and citric acid. Mineral acids, e.g., hydrochloric acid, are also useful for this purpose. The amounts of aluminum amalgam and acetic acid are not critical provided that sufficient molecular equivalents of each are used to reduce each molecular equivalent of adduct. It is preferred, however, to use a large excess of aluminum amalgam and the acid, for example, acetic acid. The amount of water is also not critical, sufficient being used to provide an ionizing reaction system. Also, sufficient of a water-miscible inert organic liquid diluent is used to provide a mobile and substantially homogeneous reaction mixture except with regard to the aluminum amalgam.

The 9-methylene intermediate of formula XXI formed by the above described procedure (steps 2 and 3), may still have protective silyl groups at positions 11 and 15 if the adduct from step 2 was not desilylated before proceeding with step (3). These silyl groups are easily removed if desired before proceeding to the transformation of intermediate XXI to XXII (Chart II) by mixing the silylated intermediate XXI with dilute aqueous citric acid, phosphoric acid, or some other appropriate acid as described above. This desilylation is not essential since the next step, i.e., step (4) in Chart II is a silylation to protect the same hydroxy groups and the carboxyl group if present, before proceeding with steps (5), (6) and (7) of Chart II. But if it is desired to isolate and purify intermediate XXI before proceeding to intermediate XXII, it is preferable that XXI be isolated and purified in a desilylated form.

Referring again to Chart II, intermediate XXI is transformed to intermediate XXII by the four steps, (4), (5), (6), and (7) shown in Chart II.

The silylation step (4), if silyl groups are not already present after the transformation of XX to XXI, is carried out as described above for step (1) of Chart II. For this silylation, however, preferred silyl groups are triphenylsilyl and t-butyldimethylsilyl.

Step (5) in Chart II is a combination of hydroboration and oxidation which transforms the 9-methylene group of XXI to a 9-hydroxymethyl group (—CH$_2$OH). Hydroboration-oxidation processes are known in the art for hydrating olefinic double bonds. See, for example, Zweifel et al., "Organic Reactions", Volume 13, Chapter 1, John Wiley and Sons, Inc., New York (1963). An especially suitable hydroboration reagent for step (5) of Chart II is 9-borabicyclo[3.3.1]nonane, also known as 9-BBN. See Knights et al., J. Am. Chem. Soc. 90, 5280 (1968); ibid, 5281. Procedures useful for the hydroboration and the subsequent oxidation of silylated XXI are as described in the art, for example, Zwiefel et al. and Knights et al., above cited. See also Brown et al., J. Am. Chem. Soc. 96, 7765 (1974).

Step (6) in Chart II is the formation of the sulfonic acid ester of the primary alcohol (9-CH$_2$OH) resulting from step (5). This step (6) is carried out as described above for the formation of sulfonic acid ester XVIII (Chart I), using sulfonyl halides within the scope of R$_5$SO$_2$X wherein R$_5$ and X are as defined above. For this step (6) of Chart II, however, methanesulfonyl chloride is especially preferred, its use yielding the methanesulfonic acid ester.

Referring again to Chart II, the next step, i.e., step (7), is the removal or desilylation of the protective silyl groups of the sulfonic acid ester prepared by preceeding step (6). This is accomplished as described above for the earlier desilylation reaction involved in Chart II, namely contacting the sulfonic acid ester with an appropriate acid, for example, aqueous solutions of citric acid or phosphoric acid, especially the latter when the silyl group is triphenylsilyl.

Finally in Chart II, the transformation of sulfonic acid ester intermediate XXII to cyclic ether final product XXIII is carried out as described above for the Chart I transformation of sulfonic acid intermediate XVIII to cyclic ether final product XIX, namely by reaction of XXII with a base.

As described above, when a cyclic ether final product of formulas XIX or XXIII wherein R$_1$ is hydrogen is desired for one of the above-described pharmacological purposes, it is preferred that the corresponding methyl or ethyl ester be prepared according to Charts I or II, starting with formula XV or XX initial reactants wherein R$_1$ is methyl or ethyl, respectively, and that the final ester be saponified to the free acid by procedures known in the art. An alternative preference is to transforms sulfonic acid ester intermediate methyl or ethyl ester XVIII or XXII to XIX or XXIII, respectively, with an aqueous alkali metal hydroxide, especially sodium or potassium hydroxide. Thereby, the cyclic ether grouping is formed and the methyl or ethyl ester grouping saponified in a single reaction step.

The novel cyclic ethers of formulas IV, V, and VI are prepared by the process shown in Chart III.

CHART III

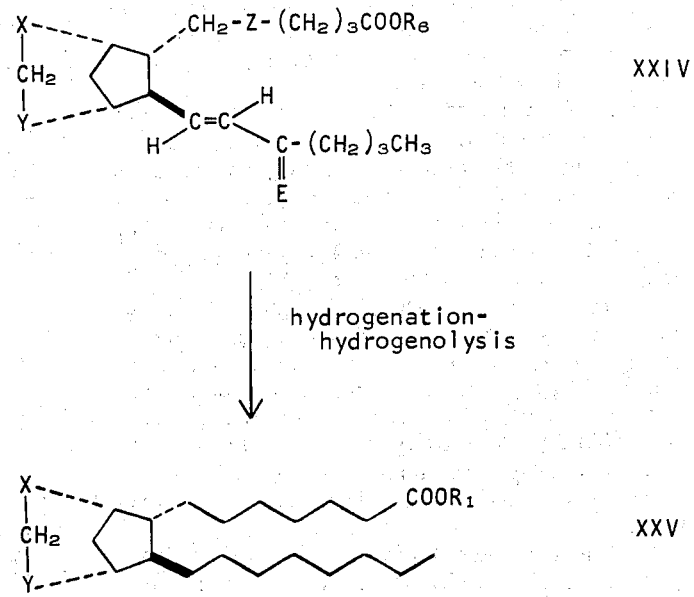

In Chart III, X, Y, and Z are as defined above, R$_1$ is hydrogen or alkyl of one to 4 carbon atoms, inclusive, R$_6$ is alkyl of one to 4 carbon atoms, inclusive, and E is

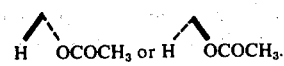

In other words, in the Chart III process, one starts with an alkyl ester 15-acetate of a cyclic ether prepared as described above in Chart I or Chart II except that it is preferred to make reactant XXIV by acetylation in the usual way from a formula XXIV compound wherein E is

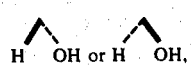

also prepared as in Chart I or Chart II, rather than by making the formula XXIV acetate reactant directly by the processes of Charts I or II, using an acetate reactant at some stage in those processes. The latter procedure is, however, operable.

The transformation of acetate reactant XXIV to desired product XXV is a combination hydrogenation and hydrogenolysis, the C-13,C-14 carbon-carbon double bond being transformed to a single bond and, when Z is cis-CH=CH—, that being transformed to —CH₂CH₂—, and E being transformed to

This transformation is carried out by hydrogenation in the presence of a hydrogenation catalyst, for example, one of the usual catalytic forms of palladium or platinum, and preferably in the presence of a small amount of a mineral acid, for example, hydrochloric acid. The choice of specific reaction conditions, for example, temperature, pressure, diluent, and duration are all within the skill of this art.

When a formula XXV product wherein $R_1$ is alkyl of one to 4 carbon atoms, inclusive, is desired, it is preferred to use a formula XXIV reactant wherein $R_6$ is that same alkyl. When a formula XXV product wherein $R_1$ is hydrogen is desired, it is preferred that the formula XXIV reactant be a methyl ester, i.e., $R_6$ is methyl, and that the methyl ester of XXV not be isolated from the hydrogenation-hydrogenolysis reaction mixture but rather be saponified in the usual manner by adding a strong base, for example, aqueous sodium or potassium hydroxide solution, to the reaction mixture after removal of the hydrogenation catalyst, for example, by filtration or centrifugation. Then, after saponification is complete, the mixture is acidified, and the formula XXV product isolated by procedures known in the art.

When an alkyl ester of a formula XIX, XIII, or XXV product, i.e., $R_1$ is alkyl of one to 4 carbon atoms, inclusive, is desired for one of the above-described pharmacological purposes, that ester is prepared starting with formula XV, XX, or XXIV initial reactants wherein $R_1$ is the desired alkyl group, avoiding aqueous base in the last step of each process sequence as described above. Alternatively, the desired alkyl ester is prepared from the formula XIX, XXIII, or XXV final product wherein $R_1$ is hydrogen by procedures known in the art. For example, this esterification is readily accomplished by interaction of the free acid with the appropriate diazohydrocarbon. For example, when diazomethane is used, the methyl esters are produced. Similar use of diazoethane, diazopropane, and diazobutane, for example, gives the ethyl, propyl, and butyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactant with the diazohydrocarbon be no longer than necessary to effect the desired esterification, preferably about one to about ten minutes, to avoid undesired molecular changes. Diazohydrocarbons are known in the art or are prepared by methods known in the art. See, for example, Organic Reactions, John Wiley & Sons, Inc., New York, N. Y., Vol. 8, pp. 389–394 (1954).

An alternative method for esterification of the free acid forms of the formula XIX, XXIII, or XXV compounds comprises transformation of the acid to the corresponding silver salt followed by interaction of that salt with an alkyl iodide.

Examples of suitable iodides are methyl iodide, ethyl iodide, butyl iodide, isobutyl iodide, tert-butyl iodide, and the like. The silver salts are prepared by conventional methods, for example, by slowly neutralizing the acid with slightly less than the stoichiometric amount of cold dilute aqueous ammonia, and then adding the stoichiometric amount of silver nitrate.

The final compounds of formulas I, II, III, IV, V, and VI wherein R is a pharmacologically acceptable cation are prepared from the corresponding free acids (R is hydrogen) by a variety of procedures known in the art, for example, neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium salts, amine acid addition salts, and quaternary ammonium salts. The choice of procedure depends in part upon the solubility characteristics of the particular salt to be prepared. In the case of the inorganic salts, it is usually suitable to dissolve the acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired. To produce an amine salt, the formula I–VI acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the formula I to VI acid with the stoichiometric amount of the corresponding quaternary ammonium hydroxide in water solution, followed by evaporation of the water.

In addition to being useful as intermediates in the novel Chart II processes, the 9-deoxy-9-methylene-PGE-type compounds of formula XXI are also useful as gastric antisecretory agents for the treatment of mammals, including man, dogs, and pigs. Especially useful for this purpose are the compounds of formula XXI wherein $R_2$ and $R_3$ are methyl and A is

and wherein $R_2$ and $R_3$ are hydrogen, and A is

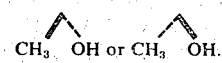

These compounds are used to treat gastric secretory medical problems as described in the art for other prostaglandin-like compounds. See, for example, German Offenlegungsschrift 2,216,717. Somewhat larger doses of the formula XXI compounds of this invention are usually used for this purpose than those described for the prostaglandin-like compounds in said 2,216,717. In particular, for the preferred formula XXI compounds mentioned above, doses in the range about 2 to about 10 times the doses described in 2,216,717 are used. For the other formula XXI compounds, dose in the range about 5 to about 20 times the doses described in 2,216,717 are used.

The invention can be more fully understood by the following examples.

Infrared absorption spectra are recorded on a Perkin-Elmer model 421 infrared spectrophotometer, using undiluted (neat) samples or mineral oil mulls. NMR spectra are recorded on a Varian A-60A spectrophotometer in deuterochloroform solutions with tetramethylsilane as an internal standard. Mass spectra are recorded on an Atlas CH-4 mass spectrometer with a TO-4 source (ionization voltage 70 ev).

Example 1: 11-Deoxy-11α-hydroxymethyl-PGE$_1$
(Formula XVI; R$_1$, R$_2$, R$_3$=H;

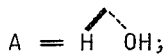

Z=—CH$_2$CH$_2$—).

A solution of PGA$_1$ (3.36 g.) and benzophenone (300 mg.) in 900 ml. of methanol is irradiated in a Rayonet type RS preparative photochemical reactor using 3500 A light with cooling in the range 28° to 32° C., stirring and excluding oxygen with a stream of nitrogen introduced into the bottom of the reactor via a gas dispersion tube. After a reaction period of 2.5 hours, additional benzophenone (300 mg.) is added. Then after each of two further reaction periods of one hour each, additional benzophenone (300 mg.) is added. One hour later, thin layer chromatographic analysis of a portion of the reaction mixture with the A-IX solvent system (Hamberg et al., J. Biol. Chem. 241,257 (1966)) shows that the reaction mixture contains no detactable amount of the PGA$_1$ reactant. The excess methanol is then evaporated under reduced pressure, and the residue is chromatographed on a silica gel column (700 g. of Mallinckrodt CC-4) packed with Skellysolve B (a mixture of isomeric hexanes) containing 25 percent by volume of ethyl acetate, eluting the column successively with 10 l. of ethyl acetate-Skellysolve B (1:1 by volume), 10 l. of ethyl acetate-Skellysolve B (3:1 by volume), and 10 l. of ethyl acetate, collecting 450-ml. fractions. Fractions 46–54 are combined and evaporated under reduced pressure to give 1.10 g. of the desired 11-deoxy-11α--hydroxymethyl-PGE$_1$; infrared absorption at 3340, 2650, 1730, 1460, 1375, 1250, 1160, 1050, and 972 cm$^{-1}$; NMR peaks at 5.7–5.4 (multiplet), 4.75–4.3 (multiplet), 4.25–3.90 (multiplet), and 3.75–3.5 (multiplet)δ. Earlier chromatographic fractions contain additional amounts of the desired product mixed with small amounts of the corresponding 11β-isomer. Additional amounts of the desired 11α-product are obtained from the earlier fractions by further chromatographic procedures as described hereinabove using appropriate gradients of ethyl acetate and Skellysolve B.

Example 2: 11-Deoxy-11α-hydroxmethyl-PGE$_2$
(Formula XVI; R$_1$, R$_2$, R$_3$=H; -hydroxymethyl-PGE

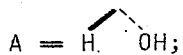

Z=cis—CH=CH—).

A solution of PGA$_2$ (10.00 g.) and benzophenone (5.40 g.) in 1000 ml. of methanol is irradiated in a Raynot type RS preparative photochemical reactor using 3500 A light with cooling, stirring, and a nitrogen atmosphere as described in Example 1. After a 5-hour irradiation time, the excess methanol is evaporated under reduced pressure. The resulting residue is chromatographed on a silica gel column (1500 g. of Mallinckrodt CC-4) packed with ethyl acetate-Skellysolve B (1:3 by volume), eluting successively with 10 l. of ethyl acetate-Skellysolve B (1:1 by volume), 10 l. of an ethyl acetate-Skellysolve B gradient starting at 1:1 by volume and ending at 4:1 by volume, 10 l. of an ethyl acetate-Skellysolve B gradient starting at 4:1 by volume and ending with pure ethyl acetate, and 10 l. of pure ethyl acetate, collecting 350-ml. fractions. Fractions 57–79 are combined and evaporated under reduced pressure to give 1.37 g. of the desired 11-deoxy- 11α-hydroxymethyl-PGE$_2$; infrared absorption at 3400, 2650, 1725, 1455, 1405, 1375, 1235, 1160, 1105, 1055, 1020, and 970 cm$^{-1}$; NMR peaks at 5.74–5.10 (multiplet), 5.35 (broad singlet), 4.35–3.95 (multiplet), and 3.90–3.50 (broad singlet) δ. Earlier chromatographic fractions 48–56 contain additional amounts of the desired product mixed with small amounts of the corresponding 11β-isomer. Additional amounts of the desired 11α-product are obtained by rechromatography of the residue (6.82 g.) obtained by evaporation of these earlier fractions 48–56 under reduced pressure. For this second chromatography, the procedure described above is used (1.3 kg. of CC-4 silica), fractions 76–85 being combined and evaporated under reduced pressure to give an additional 3.63 g. of 11-deoxy-11α-hydroxymethyl-PGE$_2$.

Example 3: 11-Deoxy-11α-hydroxymethyl-PGE$_1$ Methyl Ester.

A cold (0° C.) diethyl ether solution of diazomethane (prepared from 2.6 g. N-methyl-N-nitro-N-nitrosoguanidine) is added to a solution of 11-deoxy-11α-hydroxymethyl-PGE$_1$ (1.35 g.; contains about 15 percent of the 11β-isomer) in 20 ml. of methanol at 0° C. After 5 minutes at 0° C., acetic acid is added to react with the excess diazomethane, and the total reaction mixture is evaporated under reduced pressure. The residue is dissolved in diethyl ether, and the solution is washed successively with aqueous sodium bicarbonate solution and brine (saturated aqueous sodium chloride solution), and is then evaporated under reduced pressure. The residue is chromatographed on 170 g. of neutral silica (E. Merck), packing and eluting the column with ethyl acetate, and collecting 17-ml. fractions. Fractions 48–110 are combined and evaporated to give 768 mg. of 11-deoxy-11α-hydroxymethyl-PGE$_1$ methyl ester; homogeneous by thin layer chromatograhy (tlc); R$_f$ 0.16 in ethyl acetate. This material crystallized on trituration, and is recrystallized from a mixture of ethyl acetate and hexane to give 540 mg. of the same methyl ester; m.p. 47.8°–48.3° C.; infrared absorption at 3400, 1735, 1290, 1220, 1190, 1170, 1075, 1025, and 980 cm$^{-1}$; NMR peaks at 5.75–5.45 (multiplet), 4.3–3.9 (multiplet), 3.67 (singlet), and 2.45 (singlet) δ.

Example 4: 11-Deoxy-11α-hydroxymethyl-PGE$_2$ Methyl Ester.

Following the procedure of Example 3, 11-deoxy-11α-hydroxymethyl-PGE$_2$ (containing a minor amount of the 11β-isomer) is treated with excess diazomethane, and the product (1.2 g.) is chromatographed on 200 g. of neutral silica (E. Merck), packing with ethyl acetate-Skellylsolve B (9:1 by volume) and eluting successively with 1 l. of ethyl acetate-Skellysolve B (9:1 by volume) and 3 l. of ethyl acetate, collecting 50-ml. fractions. Fractions 111–140 are combined and evaporated to give 580 mg. of 11-deoxy-11α-hydroxymethyl-PGE$_2$ methyl ester; homogeneous on tlc; infrared absorption at 3480, 1745, 1725 (sh), 1440, 1375, 1160, 1060, and 976 cm$^{-1}$; NMR peaks at 5.8–5.56 (multiplet), 5.56–5.25 (multiplet), 4.3–3.85 (multiplet), 3.68 (singlet), and 2.60 (singlet) δ.

Example 5: 11-Deoxy-11α-hydroxymethyl-PGE$_1$ Methyl Ester.

Following the procedure of Example 1 but using PGA$_1$ methyl ester in place of PGA$_1$, there is obtained 11-deoxy-11α-hydroxy-methyl-PGE$_1$ methyl ester; substantially the same physical properties as the product of Example 3.

Example 6: 11-Deoxy-11α-hydroxymethyl-PGE$_2$ Methyl Ester.

Following the procedure of Example 2 but using PGA$_2$ methyl ester in place of PGA$_2$, there is obtained 11-deoxy-11α-hydroxymethyl-PGE$_2$ methyl ester; substantially the same physical properties as the product of Example 4.

Example 7: 11-Deoxy-11α-hydroxymethyl-15β-PGE$_1$.

Following the procedures of Examples 1 and 2 but using 15β-PGA$_1$ in place of PGA$_1$ and PGA$_2$, there is obtained 11-deoxy-11α-hydroxymethyl-15β-PGE$_1$.

Example 8: 11-Deoxy-11α-hydroxymethyl-15β-PGE$_1$ Methyl Ester.

Following the procedure of Example 3 but using 11-deoxy-11α-hydroxymethyl-15β-PGE$_1$ in place of 11-doexy-11α-hydroxymethyl-PGE$_1$, there is obtained 11-deoxy-11α-hydroxymethyl-15β-PGE$_1$ methyl ester. Also following the procedures of Examples 1 and 2 but using 15β-PGA$_1$ methyl ester in place of PGA$_1$ and PGA$_2$, there is obtained 11-deoxy-11α-hydroxymethyl-15β-PGE$_1$ methyl ester with substantially the same physical properties.

Example 9: 11-Deoxy-11α-hydroxymethyl-15β-PGE$_2$

Following the procedures of Examples 1 and 2 but using 15β-PGA$_2$ in place of PGA$_1$ and PGA$_2$, there is obtained 11-deoxy-11α-hydroxymethyl-15β-PGE$_2$.

Example 10: 11-Deoxy-11α-hydroxymethyl-15β-PGE$_2$ Methyl Ester.

Following the procedure of Example 3 but using 11-deoxy-11α-hydroxymethyl-15β-PGE$_2$ in place of 11-deoxy-11α-hydroxymethyl-PGE$_1$, there is obtained 11-deoxy-11α-hydroxymethyl-15β-PGE$_2$ methyl ether. Also following the procedures of Examples 1 and 2 but using 15β-PGA$_2$ methyl ester in place of PGA$_1$ and PGA$_2$, there is obtained 11-deoxy-11α-hydroxymethyl-15β-PGE$_2$ methyl ester with substantially the same physical properties.

Example 11: 11-Deoxy-11α-hydroxymethyl-PGE$_2$ Methyl Ester 15-Acetate.

A solution of PGA$_2$ methyl ester 15-acetate (10.00 g.) and benzophenone (5.00 g.) in 1000 ml. of methanol is irradiated four hours in a Rayonet type RS preparative photochemical reactor using 3500 A light with cooling in accord with the procedures of Examples 1 and 2. The excess methanol is then evaporated under reduced pressure, and the residue is combined with the residue (837 mg.) obtained from a previous similar but smaller scale irradiation of PGA$_2$ methyl ester 15-acetate. The combined residues are chromatographed on 1.5 kg. of neutral silica, packing with ethyl acetate-Skellysolve B (3:7 by volume) and eluting successively with 4 l. of ethyl acetate-Skellysolve B (3:7 by volume), 28 l. of ethyl acetate-Skellysolve B (4:6 by volume, and 2 l. of ethyl acetate-Skellysolve B (8:2 by volume), collecting 150-ml. fractions. Fractions 95–125 are combined and evaporated under reduced pressure to give 4.35 g. of 11-deoxy-11α-hydroxymethyl-PGE$_2$ methyl ester 15-acetate; infrared absorption at 3500, 1745, 1735 (sh), 1360, 1230, 1160, 1020, 970, and 895 cm$^{-1}$; NMR peaks at 5.75–5.00 (multiplet), 3.65 (singlet), 2.80 (singlet), and 2.02 (singlet)δ.

Example 12: 11-Deoxy-11α-hydroxymethyl-15β-PGE$_2$ Methyl Ester 15-Acetate.

Following the procedure of Example 11 but using 15β-PGA$_2$ methyl ester 15-acetate in place of PGA$_2$ methyl ester 15-acetate, there is obtained 11-deoxy-11α-hydroxymethyl-15β-PGE$_2$ methyl ester 15-acetate.

Example 13:
11-Deoxy-11α-hydroxymethyl-16,16-dimethyl-PGE$_2$ and its Methyl Ester.

Following the procedures of Examples 1 and 2 but using 16,16-dimethyl-PGA$_2$ in place of PGA$_1$ and PGA$_2$, there is obtained 11-deoxy-11α-hydroxymethyl-16,16-dimethyl-PGE$_2$. Also following the procedure of Example 3 but using 11-deoxy-11α-hydroxymethyl-16,16-dimethyl-PGE$_2$ in place of 11-deoxy-11α-hydroxymethyl-PGE$_1$, there is obtained 11-deoxy-11α-hydroxymethyl-16,16-dimethyl-PGE$_2$ methyl ester. Following the procedures of Examples 1 and 2, the same methyl ester with substantially the same physical properties is obtained by using 16,16-dimethyl-PGA$_2$ methyl ester in place of PGA$_1$ and PGA$_2$.

Example 14:
11-Deoxy-11α-hydroxymethyl-15α-methyl-PGE$_2$ and its Methyl Ester.

Following the procedures of Examples 1 and 2 but using 15α-methyl-PGA$_2$ in place of PGA$_1$ and PGA$_2$, there is obtained 11-deoxy-11α-hydroxymethyl-15α-methyl-PGE$_2$. Also following the procedure of Example 3 but using 11-deoxy-11α-hydroxymethyl-15α-methyl-PGE$_2$ in place of 11-deoxy-11α-hydroxymethyl-PGE$_1$, there is obtained 11-deoxy-11α-hydroxymethyl-15α-methyl-PGE$_2$ methyl ester. Following the procedures of Examples 1 and 2, the same methyl ester with substantially the same physical properties is obtained by using 15α-methyl-PGA$_2$ methyl ester in place of PGA$_1$ and PGA$_2$.

Also following the procedures of Examples 1 and 2, 15α-ethyl-PGA$_1$, 15α-ethyl-PGA$_2$, 15β-methyl-PGA$_1$, 15β-methyl-PGA$_2$, 15β-16,16-dimethyl-PGA$_1$, 15β-16,16-dimethyl-PGA$_2$, 16-methyl-PGA$_1$, 16-methyl-PGA$_2$, 15β-16-methyl-PGA$_2$, and the methyl esters of each of those, are transformed to 11-deoxy-11α-hydroxymethyl-15α-ethyl-PGE$_1$, 11-deoxy-11α-hydroxymethyl-15α-ethyl-PGE$_2$, 11-deoxy-11α-hydroxymethyl-15β-methyl-PGE$_1$, 11-deoxy-11α-hydroxymethyl-15β-methyl-PGE$_2$, 11-deoxy-11α-hydroxymethyl-15β-16,16-dimethyl-PGE$_1$, 11-deoxy-11α-hydroxymethyl-15β-16,16-dimethyl-PGE$_2$, 11-deoxy-11α-hydroxymethyl-16-methyl-PGE$_1$, 11-deoxy-11α-hydroxymethyl-16-methyl-PGE$_2$, 11-deoxy-11α-hydroxymethyl-15β-16-methyl-PGE$_2$, and the methyl esters of each of those, respectively.

Further following the procedures of Examples 1 and 2, 11-deoxy-11α-hydroxymethyl-PGE$_1$ ethyl ester, propyl ester, isopropyl ester, butyl ester, isobutyl ester, sec.-butyl ester, and tert.-butyl ester are prepared by using PGA$_1$ ethyl ester, propyl ester, isopropyl ester, butyl ester, isobutyl ester, sec.-butyl ester, and tert.-butyl ester, respectively, in place of PGA$_1$ and PGA$_2$. Also following the procedures of Examples 1 and 2, each of the alkyl esters of 2, 3, and 4 carbon atoms in the alkyl moiety of 11-deoxy-11α-hydroxymethyl-PGE$_2$, 11-deoxy-11α-hydroxymethyl-16,16-dimethyl-PGE$_2$, and 11-deoxy-11α-hydroxymethyl-15α-methyl-PGE$_2$ are prepared by using each of the corresponding alkyl esters of PGA$_2$, 16,16-dimethyl-PGA$_2$, and 15α-methyl-PGA$_2$, respectively. Further, also following the procedures of Examples 1 and 2, each of the alkyl esters of 2, 3, and 4 carbon atoms in the alkyl moiety of each of the other PGA$_1$-type and PGA$_2$-type compounds mentioned above is prepared.

Example 15: 11-Deoxy-11α-hydroxymethyl-PGF$_1$ α (Formula XVII; R$_1$, R$_2$, R$_3$=H;

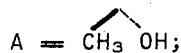

Z=-CH$_2$CH$_2$—).

A solution of 11-deoxy-11α-hydroxymethyl-PGE$_1$ (400 mg.) in 200 ml. of tetrahydrofuran is added gradually during 10 minutes to 20 ml. of a stirred 0.6 N solution of lithium perhydro-9b-boraphenalylhydride in diglyme at about −78° C. The resulting mixture is stirred 3 hours at −78° C. and is then allowed to warm to 20° C. during 30 minutes. To the mixture are then added successively water (3 ml.; added slowly), 1 N hydrochloric acid (15 ml.), and water (300 ml.). The resulting mixture is extracted several times with ethyl acetate, and the combined ethyl acetate extracts are extracted three times with 0.5 M aqueous sodium carbonate solution. The combined aqueous extracts are washed once with ethyl acetate, acidified with 2N aqueous potassium bisulfate solution, and then extracted several times with ethyl acetate. The combined ethyl acetate extracts are washed with brine, dried with anhydrous sodium sulfate, and evaporated under reduced pressure. The residue (1.04 g.) is chromatographed on 50 g. of silica (Mallinckrodt CC-4), the column being packed with ethyl acetate-hexane (6:4 by volume) and eluted successively with 1 l. of ethyl acetatehexane (6:4 by volume) and a gradient of 1 l. of ethyl acetate-hexane (6:4 by volume) and 1 l. of ethyl acetate, collecting 15-ml. fractions. Fractions 164–250 are combined and evaporated under reduced pressure to give 0.375 g. of 11-deoxy-11α-hyroxymethyl-PGF$_1$ α which crystallized on trituration and which is recyrstallized three times from a mixture of ethyl acetae and hexane; m.p. 73°–74° C.; infrared absorption at 3430, 3230, 2700, 1700, 1305, 1280, 1240, 1200, 1025, 1000, 985, and 965 cm$^{-1}$.

Example 16: 11-Deoxy-11α-hydroxymethyl-PGF$_1$ α Methyl Ester.

Lithium tri-(t-butoxy)-aluminohydride (1.3 g.) is added slowly to a solution of 11-deoxy-11α-hydroxymethyl-PGE$_1$ methyl ester (0.490 g.) in 20 ml. of tetrahydrofuran. The mixture is stirred for 18 hours at about 25° C. Then the mixture is evaporated under reduced pressure, and both water and diethyl ether are added to the residue. This mixture is acidified with aqueous 2N potassium bisulfate solution and extractd several times with diethyl ether. The combined extracts are washed successively with aqueous sodium bicarbonate solution and water, dried with anhydrous sodium sulfate, and evaporated under reduced pressure. The residue (0.510 g.) is chromatographed on 50 g. of neutral silica, packing the column with acetone-dichloromethane (1:9 by volume), and eluting successively with 250 ml. of acetone-dichloromethane (3:7 by volume), 250 ml. of acetone-dichloromethane (35:65 by volume), and 1.5 l. of acetone-dichloromethane (1:1 by volume) collecting 15-ml. fractions. Fractions 38–48 are combined on the basis of tlc homogeniety (acetone-dichloromethane 4:6; R$_f$ 0.39) and evaporated to give 0.150 g. of 11-deoxy-11α-hydroxymethyl-PGF$_1$ α methyl ester; NMR peaks at 5.56–5.35 (multiplet), 4.25–3.90 (multiplet), 3.67 (singlet), 3.65–3.45 (multiplet), and 3.40 (singlet) δ.

Example 17: 11-Deoxy-11α-hydroxymethyl-PGF$_2$ α (Formula XVII; R$_1$, R$_2$, R$_3$=H;

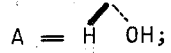

Z=cis-CH=CH—).

A solution of 11-deoxy-11α-hydroxymethyl-PGE$_2$ (1.13 g.) in 50 ml. of tetrahydrofuran is added gradually during 10 minutes to 25 ml. of a stirred 0.6 M solution of lithium perhydro-9b-borophenalylhydride in diglyme at about −78° C. The resulting mixture is stirred 2 hours at −78° C. and is then allowed to warm to 20° C. during 60 minutes. To the mixture are then added successively water (3 ml.; added slowly), 2N aqueous potassium bisulfate solution (15 ml.), and water (300 ml.). The resulting mixture is extracted several times with ethyl acetate, and the combined ethyl acetate extracts are washed once with water and then extracted three times with 50-ml. portions of 0.5M aqueous sodium carbonate solution. The combined aqueous extracts are washed once with ethyl acetate, acidified with 2N potassium bisulfate solution, and the extracted several times with ethyl acetate. The combined ethyl acetate extracts are washed with brine, dried with anhydrous sodium sulfate, and evaporated under reduced pressure. The residue (1.2 g.) is combined with the corresponding residue from a separate reaction of the same size, and this (2.46 g.) is chromatographed on 200 g. of silica (Mallinckrodt CC-4), the column being packed with ethyl acetate-Skellysolve B (6:4 by volume) and eluted successively with 1 l. ethyl acetate-Skellysolve B (8:2 by volume), 1 l. ethyl acetate-Skellysolve B (9:1 by volume), and 1 l. ethyl acetate, collecting 23-ml. fractions. Fractions 35–47 are combined and evaporated under reduced pressure to give 1.14 g. of 11-deoxy-11α-hydroxymethyl-PGF$_2$ $_\alpha$ which crystallized on standing and is recrystallized from a mixture of ethyl acetate and hexane; m.p. 64°–65° C.; infrared absorption at 3220, 2720, 2680, 1715, 1325, 1270, 1200, 1025, 990, 965, and 940 cm.$^{-1}$; NMR peaks at 5.75–5.05 (multiplet), 4.3–3.85 (multiplet), and 3.8–3.3 (multiplet) δ.

Example 18: 11-Deoxy-11α-hydroxymethyl-PGF$_2$ $_\alpha$ Methyl Ester.

A solution of 11-deoxy-11α-hydroxymethyl-PGF$_{2\alpha}$ (300 mg.) in diethyl ether is mixed with a solution of a molecular excess of diazo-methane in diethyl ether at 0° C. for about 5 minutes. The reaction mixture is then evaporated under reduced pressure, and the residue is chromatographed on 80 g. of neutral silica, packing with ethyl acetate-hexane (6:4 by volume), and eluting successively with 500 ml. ethyl acetate-hexane (6:4 by volume), 500 ml. ethyl acetate-hexane (7:3 by volume), and 2 l. ethyl acetate-hexane (8:2 by volume), collecting 10-ml. fractions. Fractions 120–190 are combined and evaporated under reduced pressure to give 209 mg. of 11-deoxy-11α-hydroxymethyl-PGF$_2$ $_\alpha$ methyl ester; crystallized from a mixture of ethyl acetate and hexane; m.p. 47°–51° C.; infrared absorption at 3240, 1740, 1670, 1440, 1245, 1195, 1175, 1025, 1010, 990, and 965 cm$^{-1}$; NMR peaks at 5.70–5.25 (multiplet), 4.26–3.90 (multiplet), 3.68 (singlet), and 2.70 (singlet) δ.

EXAMPLE 19:
11-Deoxy-11α-hydroxymethyl-PGF$_1$ $_\alpha$ Methyl Ester.

Following the procedure of Example 18, 11-deoxy-11α-hydroxymethyl-PGF$_1$ $_\alpha$ is transformed to 11-deoxy-11α-hydroxymethyl-PGF$_1$ $_\alpha$ methyl ester; substantially the same physical properties as the product of Example 16.

Example 20: 11-Deoxy-11α-hydroxymethyl-PGF$_2$ $_\alpha$ Methyl Ester.

Following the procedure of Example 16 but using 11-deoxy-11α-hydroxymethyl-PGE$_2$ methyl ester in place of 11-deoxy-11α-hydroxymethyl-PGE$_1$ methyl ester, there is obtained 11-deoxy-11α-hydroxymethyl-PGF$_2$ $_\alpha$ methyl ester; substantially the same physical properties as the product of Example 18.

Example 21:
11-Deoxy-11α-hydroxymethyl-15β-PGF$_1$ $_\alpha$ .

Following the procedures of Examples 15 and 17 but using 11-deoxy-11α-hydroxymethyl-15β-PGE$_1$ in place of the reactants of Examples 15 and 17, there is obtained 11-deoxy-11α-hydroxymethyl-15β-PGF$_1$ $_\alpha$ .

Example 22:
11-Deoxy-11α-hydroxymethyl-15β-PGF$_1$ $_\alpha$ Methyl Ester.

Following the procedure of Example 18 but using 11-deoxy-11α-hydroxymethyl-15β-PGF$_1$ $_\alpha$ in place of the reactant of Example 18, there is obtained 11-deoxy-11α-hydroxymethyl-15β-PGF$_1$ $_\alpha$ methyl ester. Also following the procedure of Example 16 but using 11-deoxy-11α-hydroxymethyl-15β-PGE$_1$ methyl ester in place of the reactant of Example 16, there is obtained 11-deoxy-11α-hydroxymethyl-15β-PGF$_1$ $_\alpha$ methyl ester with substantially the same physical properties.

Example 23:
11-Deoxy-11α-hydroxymethyl-15β-PGF$_2$ $_\alpha$ .

Following the procedure of Examples 15 and 17 but using 11-deoxy-11α-hydroxymethyl-15β-PGE$_2$ in place of the reactants of Examples 15 and 17, there is obtained 11-deoxy-11α-hydroxy-methyl15β-PGF$_2$ $_\alpha$ .

Example 24:
11-Deoxy-11α-hydroxymethyl-15β-PGF$_2$ $_\alpha$ Methyl Ester.

Following the procedure of Example 18, but using 11-deoxy-11α-hydroxymethyl-15β-PGF$_2$ $_\alpha$ in place of the reactant of Example 18, there is obtained 11-deoxy-11α-hydroxymethyl-15β-PGF$_2$ $_\alpha$ methyl ester. Also following the procedure of Example 16 but using 11-deoxy-11α-hydroxymethyl-15β-PGE$_2$ methyl ester in place of the reactant of Example 16, there is obtained 11-deoxy-11α-hydroxymethyl-15β-PGF$_2$ methyl ester with substantially the same physical properties.

Example 25: 11-Deoxy-11α-hydroxymethyl-PGF$_2$ $_\alpha$ Methyl Ester 15-Acetate.

Following the procedure of Example 16 but using 11-deoxy-11α-hydroxymethyl-PGE$_2$ methyl ester 15-acetate in place of the reactant of Example 16, there is obtained 11-deoxy-11α-hydroxymethyl-PGF$_2$ $_\alpha$ methyl ester 15-acetate.

Example 26:
11-Deoxy-11α-hydroxymethyl-15β-PGF$_2$ $_\alpha$ Methyl Ester 15-Acetate Following the procedure of Example 16 but using 11-deoxy-11α-hydroxymethyl-15β-PGE$_2$ methyl ester 15-acetate in place of the reactant of Example 16, there is obtained 11-deoxy-11α-hydroxymethyl-15β-PGF$_2$ $_\alpha$ methyl ester 15-acetate.

Example 27:
11-Deoxy-11α-hydroxymethyl-16,16-dimethyl-PGF$_2$ $_\alpha$ and its Methyl Ester.

Following the procedure of Examples 15 and 17 but using 11-deoxy-11α-hydroxymethyl-16,16-dimethyl-PGE$_2$ in place of the reactants of Examples 15 and 17, there is obtained 11-deoxy-11α-hydroxymethyl-16,16-dimethyl-PGF$_2$ $_\alpha$ . Also following the procedure of Example 18 but using 11-deoxy-11α-hydroxymethyl-16,16-dimethyl-PGF$_2$ $_\alpha$ in place of the reactant of Example 18 there is obtained 11-deoxy-11α-hydroxymethyl-16,16-dimethyl-PGF$_2$ $_\alpha$ methyl ester. Following the procedure of Example 16, the same methyl ester with substantially the same physical properties is obtained by using 11-deoxy-11α-hydroxymethyl-16,16-dimethyl-PGE$_2$ methyl ester in place of the reactant of Example 16.

Example 28:
11-Deoxy-11α-hydroxymethyl-15α-methyl-PGF$_2$ $_\alpha$ and its Methyl Ester.

Following the procedures of Examples 15 and 17 but using 11-deoxy-11α-hydroxymethyl-15α-methyl-PGE$_2$ in place of the reactants of Examples 15 and 17, there is obtained 11-deoxy-11α-hydroxymethyl-15α-methyl-PGF$_2$ $_\alpha$ . Aslo following the procedure of Example 18 but using 11-deoxy-11α-hydroxymethyl-15α-methyl- PGF$_{2\alpha}$ in place of the reactant of Example 18, there is obtained 11-deoxy-11α-hydroxymethyl-15α-methyl-PGF$_{2\alpha}$ methyl ester. Following the procedure of Example 16 the same methyl ester with substantially the same physical properties is obtained by using 11-deoxy-11α-hydroxymethyl-15α-methyl-PGE$_2$ methyl ester in place of the reactant of Example 16.

Also following the procedures of Examples 15, 16, and 17, 11-deoxy-11α-hydroxymethyl-15α-ethyl-PGE$_1$, 11-deoxy-11α-hydroxymethyl-15α-ethyl-PGE$_2$, 11-deoxy-11α-hydroxymethyl-15β-methyl-PGE$_1$, 11-deoxy-11α-hydroxymethyl-15β-methyl-PGE$_2$, 11-deoxy-11α-hydroxymethyl-15β-16,16-dimethyl-PGE$_1$, 11-deoxy-11α-hydroxymethyl-15β-16,16-dimethyl-PGE$_2$, 11-deoxy-11α-hydroxymethyl-16-methyl-PGE$_1$, 11-deoxy-11α-hydroxymethyl-16-methyl-PGE$_2$, 11-deoxy-11α-hydroxymethyl-15β-16-methyl-PGE$_2$, and the methyl esters of each of those are transformed to 11-deoxy-11α-hydroxymethyl-15α-ethyl-PGF$_{1\alpha}$, 11-deoxy-11α-hydroxymethyl-15α-ethyl-PGF$_{2\alpha}$, 11-deoxy-11α-hydroxymethyl-15β-methyl-PGF$_{1\alpha}$, 11-deoxy-11α-hydroxymethyl-15β-methyl-PGF$_{2\alpha}$, 11-deoxy-11α-hydroxymethyl-15β-16,16-dimethyl-PGF$_{1\alpha}$, 11-deoxy-11α-hydroxymethyl-15β-16,16-dimethyl-PGF$_{2\alpha}$, 11-deoxy-11α-hydroxymethyl-16-methyl-PGF$_{1\alpha}$, 11-deoxy-11α-hydroxymethyl-16-methyl-PGF$_{2\alpha}$, 11-deoxy-11α-hydroxymethyl-15β-16-methyl-PGF$_{2\alpha}$, and the methyl esters of each of those, respectively.

Further following the procedure of Example 16, 11-deoxy-11α-hydroxymethyl-PGF$_{1\alpha}$ ethyl ester, propyl ester, isopropyl ester, butyl ester, isobutyl ester, sec.-butyl ester, and tert.-butyl ester are prepared by using 11-deoxy-11α-hydroxymethyl-PGE$_1$ ethyl ester, propyl ester, isopropyl ester, butyl ester, isobutyl ester, sec.-butyl ester, and t-butyl ester, respectively in place of the reactant of Example 16. Also following the procedure of Example 16, each of the alkyl esters of 2, 3, and 4 carbon atoms in the alkyl moiety of 11-deoxy-11α-hydroxymethyl-PGF$_{2\alpha}$, 11-deoxy-11α-hydroxymethyl-16,16-dimethyl-PGF$_{2\alpha}$, and 11-deoxy-11α-hydroxymethyl-15α-methyl-PGF$_{2\alpha}$ are prepared by using each of the corresponding esters of the reactant of Example 16, respectively. Further, also following the procedure of Example 16, each of the alkyl esters of 2, 3, and 4 carbon atoms in the alkyl moiety of each of the other PGE$_1$-type and PGE$_2$-type compounds mentioned above is prepared.

Example 29: 11-Deoxy-11α-hydroxymethyl-PGF$_{1\alpha}$ Methyl Ester 11-Tosylate.

A solution of 11-deoxy-11α-hydroxymethyl-PGF$_{1\alpha}$ methyl ester (140 mg.) and p-toluenesulfonyl chloride (80 mg.) in 2 ml. of anhydrous pyridine is stirred at about 25° C. under nitrogen for 20 hours. The reaction mixture is then poured into a mixture of ice, water containing 15 ml. of 2N potassium bisulfate solution, and diethyl ether. The mixture is shaken and then extracted several times with diethyl ether. The combined extracts are washed successively with aqueous sodium bicarbonate solution, water, and brine, dried with anhydrous sodium sulfate, and evaporated under reduced pressure to give 130 mg. of a viscous oil. This oil is chromatographed on 15 g. of neutral silica, packing and eluting with acetone-dichloromethane (1:10 by volume), collecting 2.5-ml. fractions. Fractions 20–28 are combined and evaporated under reduced pressure to give 50 mg. of 11-deoxy-11α-hydroxymethyl-PGF$_{1\alpha}$ methyl ester 11-tosylate; NMR peaks at 7.77 and 7.36 (doublets), 5.55–5.28 (multiplet), 4.45–3.85 (multiplet), 3.67 (singlet), 2.45 (singlet), and 1.70 (singlet) δ.

Example 30 11-Deoxy-11α-hydroxymethyl-PGF$_{2\alpha}$ Methyl Ester 11-Tosylate

To a solution of 11-deoxy-11α-hydroxymethyl-PGF$_{2\alpha}$ methyl ester (725 mg.) in 10 ml. of anhydrous pyridine at 0° C., p-toluenesulfonyl chloride (405 mg.) is added in one portion with stirring. The resulting mixture is stirred at 0°–5° C. under nitrogen for 12 hours, and is then poured into a mixture of ice, water, brine, diethyl ether, and 67 ml. of 2M potassium bisulfate solution. The mixture is shaken and then extracted several times with diethyl ether. The combined extracts are washed successively with water, aqueous sodium bicarbonate solution, and brine, dried with anhydrous sodium sulfate, and evaporated under reduced pressure to give 800 mg. of residue. This residue is chromatographed on 80 g. of neutral silica (E. Merck), packing with acetone-dichloro-methane (3:97 by volume) and eluting with acetone-dichloromethane (1:9 by volume), collecting 6.5-ml. fractions. Fractions 39–59 are combined and evaporated under reduced pressure to give 445mg. of 11-deoxy-11α-hydroxymethyl-PGF$_{2\alpha}$ methyl ester 11-tosylate; R$_f$ 0.48 with acetone-dichloromethane (1:9 by volume).

Example 31:
11-Deoxy-11α-hydroxymethyl-15β-PGF$_{1\alpha}$ Methyl Ester 11-Tosylate.

Following the procedures of Examples 29 and 30 but using 11-deoxy-11α-hydroxymethyl-15β-PGF$_{1\alpha}$ methyl ester in place of the reactants of Examples 29 and 30, there is obtained 11-deoxy-11α-hydroxymethyl-15β-PGF$_{1\alpha}$ methyl ester 11-tosylate.

Example 32:
11-Deoxy-11α-hydroxymethyl-15β-PGF$_{2\alpha}$ Methyl Ester 11-Tosylate.

Following the procedures of Examples 29 and 30 but using 11-deoxy-11α-hydroxymethyl-15β-PGF$_{2\alpha}$ methyl ester in place of the reactants of Examples 29 and 30, there is obtained 11-deoxy-11α-hydroxymethyl-15β-PGF$_{2\alpha}$ methyl ester 11-tosylate.

Example 33: 11-Deoxy-11α-hydroxymethyl-PGF$_{2\alpha}$ Methyl Ester 11-Tosylate 15-Acetate.

Following the procedures of Examples 29 and 30 but using 11-deoxy-11α-hydroxymethyl-PGF$_{2\alpha}$ methyl ester 15-acetate in place of the reactants of Examples 29 and 30, there is obtained 11-deoxy-11α-hydroxymethyl-PGF$_{2\alpha}$ methyl ester 11-tosylate 15-acetate.

Example 34: 11-Deoxy-11α-hydroxymethyl-15β-PGF$_{2\alpha}$ Methyl Ester 11-Tosylate 15-Acetate.

Following the procedures of Examples 29 and 30 but using 11-deoxy-11α-hydroxymethyl-15β-PGF$_{2\alpha}$ methyl ester 15-acetate in place of the reactants of Examples 29 and 30, there is obtained 11-deoxy-11α-hydroxymethyl-15β-PGF$_{2\alpha}$ methyl ester 11-tosylate 15-acetate.

Example: 35:
11-Deoxy-11α-hydroxymethyl-16,16-dimethyl-PGF$_2$ $_\alpha$ Methyl Ester 11-Tosylate.

Following the procedure of Examples 29 and 30 but using 11-deoxy-11α-hydroxymethyl-16,16-dimethyl-PGF$_2$ $_\alpha$ methyl ester in place of the reactants OF Examples 29 and 30, there is obtained 11-deoxy-11α-hydroxymethyl-16,16-dimethyl-PGF$_2$ $_\alpha$ methyl ester 11-tosylate.

Example 36:
11-Deoxy-11α-hydroxymethyl-15α-methyl-PGF$_2$ $_\alpha$ Methyl Ester 11-Tosylate.

Following the procedure of Examples 29 and 30 but using 11-deoxy-11α-hydroxymethyl-15α-methyl-PGF$_2$ $_\alpha$ methyl ester in place of the reactants of Examples 29 and 30, there is obtained 11-deoxy-11α-hydroxymethyl-15α-methyl-PGF$_2$ $_\alpha$ methyl ester 11-tosylate.

Also following the procedures of Examples 29 and 30, the methyl esters of each of 11-deoxy-11α-hydroxymethyl-15α-ethyl-PGF$_1$ $_\alpha$, 11-deoxy-11α-hydroxymethyl-15α-ethyl-PGF$_2$ $_\alpha$, 11-deoxy-11α-hydroxymethyl-15β-methyl-PGF$_1$ $_\alpha$, 11-deoxy-11α-hydroxymethyl-15β-methyl-PGF$_2$ $_\alpha$, 11-deoxy -11α-hydroxymethyl-15β-16,16-dimethyl-PGF$_1$ $_\alpha$, 11-deoxy-11α-hydroxymethyl-15β-16,16-dimethyl-PGF$_2$ $_\alpha$, 11-deoxy-11α-hydroxymethyl-16-methyl-PGF$_1$ $_\alpha$, 11-deoxy-11α-hydroxymethyl-16-methyl-PGF$_{2\alpha}$, and 11-deoxy-11α-hydroxymethyl-15β-16-methyl-PGF$_2$ $_\alpha$, are transformed to the 11-tosylates of each of those.

Further following the procedures of Examples 29 and 30, 11-deoxy-11α-hydroxymethyl-PGF$_1$ $_\alpha$ ethyl ester, propyl ester, isopropyl ester, butyl ester, isobutyl ester, sec.-butyl ester, and tert.-butyl ester are transformed to the 11-tosylate of each of those.

Also following the procedure of Examples 29 and 30, each of the alkyl esters of 2, 3, and 4 carbon atoms in the alkyl moiety of 11-deoxy-11α-hydroxymethyl-PGF$_2$ $_\alpha$, 11-deoxy-11α-hydroxymethyl-16,16-dimethyl-PGF$_2$ $_\alpha$, and 11-deoxy-11α-hydroxymethyl-15α-methyl-PGF$_2$ $_\alpha$ is transformed to the 11-tosylate of each of those. Further, also following the procedure of Examples 29 and 30, each of the alkyl esters of 2, 3, and 4 carbon atoms, in the alkyl moiety of each of the other PGF$_1$ $_\alpha$ -type and PGF$_2$ $_\alpha$ -type compounds mentioned above is transformed to the corresponding 11-tosylate.

Example 37: 9,11-Dideoxy-9α,11α-epoxymethano-PGF$_{1\alpha}$ Methyl Ester (Formula XIX; R$_1$, R$_2$, R$_3$=H;

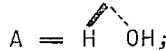

Z=—CH$_2$CH$_2$—).

A solution containing 11-deoxy-11α-hydroxymethyl-PGF$_1$ $_\alpha$ methyl ester 11-tosylate (50 mg.) and potassium tert.-butoxide (22mg.) in 5 ml. of anhydrous tetrahydrofuran is stirred under nitrogen at 25° C. for 60 minutes. The solution is then diluted with 50 ml. of diethyl ether and poured into 75 ml. of cold brine containing 5 ml. of 2N aqueous potassium bisulfate solution. This mixture is extracted three times with 75-ml. portions of diethyl ether. The combined extracts are washed successively with aqueous sodium bicarbonate solution and brine, dried with anhydrous sodium sulfate and evaporated under reduced pressure. The residue (45 mg.) is chromatographed on 20 g. of neutral silica, packing and eluting with ethyl acetane-hexane (35:65 by volume), collecting 4-ml. fractions. Fractions 37–50 are combined and evaporated under reduced pressure to give 30 mg. of 9,11-dideoxy-9α,11α-epoxymethano-PGF$_1$ $_\alpha$ methyl ester; homogenous by tlc (r$_f$ 0.21 with ethyl acetatehexane 4:6 by volume); infrared absorption at 3460, 1745, 1665, 1200, 1170, 1060, 1040, 970, 865, and 728 cm$^{-1}$; NMR peaks at 5.65–5.45 (multiplet), 4.25–3.9 (multiplet), 3.67 (singlet), 3.8–3.35 (multiplet), and 1.90 (singlet) δ.

Example 38:
9,11-Dideoxy-9α,11α-epoxymethano-PGF$_2$ $_\alpha$ (Formula XIX; R$_1$, R$_2$, R$_3$=H;

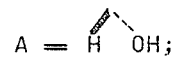

Z=cis-CH=CH—).).

Potassium tert. -butoxide (186 mg.) is added in one portion to a stirred solution of 11-deoxy-11α-hydroxymethyl-PGF$_2$ $_\alpha$ methyl ester 11-tosylate (445 mg.) in 25 ml. of anhydrous tetrahydrofuran at 25° C. After 30 minutes at 25° C., the solution is evaporated under reduced pressure, the residue is dissolved in 5 ml. of methanol, and to the methanol solution is added under nitrogen 5 ml. of 3N aqueous potassium hydroxide solution. This mixture is maintained 2 hours at 25° C., and the methanol is then removed under reduced pressure. The aqueous residue is cooled with ice, acidified with dilute aqueous potassium bisulfate solution, and extracted several times wih ethyl acetate. The combined extracts are washed with brine, dried with anhydrous sodium sulfate, and evaporated under reduced pressure. The residue (370 mg.) is chromatographed on 20 g. of acid-washed silica (Mallinckrodt CC-4), packing and eluting with ethyl acetate-hexane (35:65 by volume), collecting 3-ml. fractions. Fractions 33–64 are combined and evaporated under reduced pressure to give 225 mg. of 9,11-dideoxy-9α,11α-epoxymethano-PGF$_2$ $_\alpha$ infrared absorption at 3340, 2640, 1725 (sh), 1705, 1455, 1405, 1375, 1295, 1225, 1190, 1150, 1040, 1020, 965, 925, and 865 cm$^{-1}$; NMR peaks at 6.77 (singlet), 5.75–5.20 (multiplet), 4.35–3.86 (multiplet), 3.85–3.36 (6-line pattern), and 0.88 (triplet) δ.

Example 39:
9,11-Dideoxy-9α,11α-epoxymethano-PGF$_1$ $_\alpha$.

Following the procedure of Example 38, 11-deoxy-11α-hydroxymethyl-PGF$_1$ $_\alpha$ methyl ester 11-tosylate is transformed to 9,11-dideoxy-9α,11α-epoxymethano-PGF$_1$ $_\alpha$.

Example 40:
9,11-Dideoxy-9α,11α-epoxymethano-PGF$_2$ $_\alpha$ Methyl Ester.

Following the procedure of Example 37, 11-deoxy-11α-hydroxymethyl-PGF$_2$ $_\alpha$ methyl ester 11-tosylate is transformed to 9,11-dideoxy-9α,11α-epoxymethano-PGF$_2$ $_\alpha$ methyl ester.

Example 41:
9,11-Dideoxy-9α,11α-epoxymethano-15β-PGF$_1$ α and its Methyl Ester.

Following the procedures of Examples 37 and 38, 11-deoxy-11α-hydroxymethyl-15β-PGF$_{1\alpha}$ methyl ester 11-tosylate is transformed to 9,11-dideoxy-9α,1-1α-epoxymethano-15β-PGF$_1$ α and to its methyl ester.

Example 42:
9,11-Dideoxy-9α,11α-epoxymethano-15β-PGF$_2$ α and its Methyl Ester.

Following the procedures of Examples 37 and 38, 11-deoxy-11α-hydroxymethyl-15β -PGF$_2$ α methyl ester 11-tosylate is transformed to 9,11-dideoxy-9α,1-1α-epoxymethano-15β-PGF$_2$ α and to its methyl ester.

Example 43:
9,11-Dideoxy-9α,11α-epoxymethano-PGF$_2$ α Methyl Ester 15-Acetate.

Following the procedure of Example 37 but reducing the time of reaction with the potassium tert.-butoxide to about 15 minutes, 11-deoxy-11α-hydroxy-methyl-PGF$_2$ α methyl ester 11-tosylate 15-acetate is transformed to 9,11-dideoxy-9α,11α-epoxymethano-PGF$_2$ α methyl ester 15-acetate.

Example 44:
9,11-Dideoxy-9α,11α-epoxymethano-PGF$_2$ α .

Following the procedure of Example 38, 11-deoxy-11α-hydroxymethyl-PGF$_2$ α methyl ester 11-tosylate 15-acetate is transformed to 9,11-dideoxy-9α,11α-epoxymethano-PGF$_2$ α ; substantially the same physical properties as for the product of Example 39.

Example 45:
9,11-Dideoxy-9α,11α-epoxymethano-15β-PGF$_2$ α Methyl Ester 15-Acetate.

Following the procedure of Example 37 but reducing the time of reaction with the potassium tert.-butoxide to about 15 minutes, 11-deoxy-11α-hydroxymethyl-15β-PGF$_2$ α methyl ester 11-tosylate 15-acetate is transformed to 9,11-dideoxy-9α,11α-epoxymethano-15β-PGF$_2$ α methyl ester 15-acetate.

Example 46:
9,11-Dideoxy-9α,11α-epoxymethano-15βPGF$_2$ α .

Following the procedure of Example 38, 11-deoxy-11α-hydroxymethyl-15β-PGF$_2$ α methyl ester 11-tosylate-15-acetate is transformed to 9,11-dideoxy-9α,11α-epoxymethano-15β-PGF$_2$ α ; substantially the same physical properties as for the acid product of Example 42.

Example 47:
9,11-Dideoxy-9α,11α-epoxymethano-16,16-dimethyl-PGF$_2$ α and its Methyl Ester.

Following the procedures of Examples 37 and 38, 11-deoxy-11α-hydroxymethyl-16,16-dimethyl-PGF$_2$ α methyl ester 11-tosylate is transformed to 9,11-dideoxy-9α,11α-epoxymethano-16,16-dimethyl-PGF$_2$ α and to its methyl ester.

Example 48: 9,11-Dideoxy-9α, 11α-epoxymethano-15α-methyl-PGF$_2$ α and its Methyl Ester.

Following the procedures of Examples 37 and 38, 11-deoxy-11α-hydroxymethyl-15α-methyl-PGF$_2$ α methyl ester 11-tosylate is transformed to 9,11-dideoxy-9α,11α-epoxymethano-15α-methyl-PGF$_2$ α and to its methyl ester.

Also following the procedures of Examples 37 and 38, the methyl ester 11-deoxy-11α-hydroxymethyl-15α-ethyl-PGF$_1$ α , 11-deoxy-11α-hydroxymethyl-15α-ethyl-PGF$_2$ α , 11-deoxy11α-hydroxymethyl-15β-methyl-PGF$_1$ α , 11-deoxy-11α-hydroxymethyl-15β-methyl-PGF$_2$ α , 11-deoxy-11α-hydroxymethyl-15β-16,16-dimethyl-PGF$_1$ α , 11-deoxy-11α-hydroxymethyl-15β-16,16-dimethyl-PGF$_2$ α , 11-deoxy-11α-hydroxymethyl-16-methyl-PGF$_1$ α , 11-deoxy-11α-hydroxymethyl-16-methyl-PGF$_2$ α , and 11-deoxy-11α-hydroxy-methyl-15β-16-methyl-PGF$_2$ α are transformed to the free acid form and to the methyl ester form of the corresponding 9,11-dideoxy-9α,11α-epoxymethane-PGF$_2$-type compound.

Further following the procedure of Example 37, the 11-tosylate of each of 11-deoxy-11α-hydroxymethyl-PGF$_1$ α ethyl ester, propyl ester, isopropyl ester, butyl ester, isobutyl ester, sec.-butyl ester, and tert.-butyl ester is transformed to the corresponding ester of 9,11-dideoxy-9α,11α-epoxymethano-PGF$_1$ α . Also following the procedure of Example 37, the 11-tosylate of each of the alkyl esters of 2, 3, and 4 carbon atoms in the alkyl moiety of 11-deoxy-11α-hydroxymethyl-PGF$_2$ α , 11-deoxy- 11α-hydroxymethyl-16,16- dimethyl-PGF$_2$ α , and 11-deoxy-11α-hydroxymethyl-15α-methyl-PGF$_2$ α is transformed to the corresponding ester of each of the corresponding 9,11-dideoxy-9α,11α-epoxymethano-PGF$_2$ α -type compound. Further, also following the procedure of Example 37, the 11-tosylate of the alkyl esters of 2, 3 and 4 carbon atoms in the alkyl moiety of each of the other PGF$_1$ α -type and PGF$_2$ α -type compounds mentioned above is transformed to the corresponding ester of the corresponding 9,11-dideoxy-9α,11α-epoxymethano-PGF$_2$-type compound.

Example 49; 9-Deoxy-9-methylene-PGE$_2$ Methyl Ester (Formula XXI; R$_1$= methyl; R$_2$ and R$_3$=hydrogen;

Z=cis-CH=CH—)

A. PGE$_2$ methyl ester is transformed to PGE$_2$ methyl ester 11,15-bis-(trimethylsilyl ether) by reaction with a mixture of hexamethyldisilazane and trimethylchlorosilane according to the procedures of U.S. Pat. No. 3,651,116.

B. A tetrahydrofuran solution of methylmagnesium choride (50 ml.; 2M) is added dropwise during 20 minutes to a stirred solution of N,S-dimethyl-S-phenyl-sulfoximine (17.0 g.) in 150 ml. of anhydrous tetrahydrofuran at 0° C. The mixture is stirred 15 minutes at 0° C. and is then maintained at 0° C. while being added to a stirred solution of PGE$_2$ methyl ether 11,15-bis(-trimethylsilyl ether) (16.8 g.) in 65 ml. of tetrahydrofuran at about −78° C. during 45 minutes under nitrogen. Stirring is continued at −78° C. for 2.5 hours, and the mixture is then poured into a mixture of saturated aqueous ammonium chloride solution (500 ml.), ice, and diethyl ether. This mixture is extracted successively with two 300-ml. portions and a 200-ml. portion of diethyl ether, and the combined extracts are washed twice with brine and then dried with anhydrous sodium sulfate. Removal of the diethyl ether under reduced pressure gives a residue which is dissolved in 200 ml. of methanol. Aqueous citric acid solution (200 ml. of 2.5 percent) is added to the methanol solution, and the mixture is stirred for 30 minutes at 25° C. Brine is then added, and the mixture is extracted several times with ethyl acetate. The combined extracts are washed four times with brine, dried with anhydrous sodium sulfate, and evaporated under reduced pressure.

C. The residue from B is dissolved in 900 ml. of tetrahydrofuran. To this solution are added with stirring 140 ml. of water, 140 ml. of acetic acid, and amalgamated aluminum from 30 g. of 20 mesh aluminum metal granules, cooling externally to keep the mixture in the range 20°–25° C. After stirring the mixture one hour, diatomaceous earth (Celite) is added, and this mixture is filtered through a pad of Celite. The filter pad is washed with three 150-ml. portions of tetrahydrofuran, and the combined filtrate and washing are evaporated under reduced pressure. Brine is added to the residue, and the mixture is extracted successively with a 400-ml. portion, a 300-ml. portion, and two 200-ml. portions of ethyl acetate-hexane (4:6 by volume). The combined extracts are washed twice with 150-ml. portions of brine, and then with 0.5 M aqueous disodium hydrogen phosphate solution until successive washes are at pH 9. Then, the combined extracts are washed again with brine, dried with anhydrous sodium sulfate, and evaporated under reduced pressure to give 17.6g. of residue. This residue is chromatographed on 1.5kg. neutral silica, packing with ethyl acetate-hexane (3:7 by volume) and eluting with ethyl acetate-hexane (7.5:3.5 by volume), collecting 125-ml. fractions. Fractions 62–80 are combined and evaporated under reduced pressure to give 7.70g. of 9-deoxy-9-methylene-$PGE_2$ methyl ester; infrared absorption at 3360, 3070, 1740, 1655, 1435, 1365, 1315, 1245, 1210, 1160, 1080, 1020, 970, and 885 cm$^{-1}$; NMR peaks at 5.65–5.25 (multiplet), 4.90 (singlet), 4.2–3.4 (multiplet), and 3.65 (singlet) δ.

Example 50: 9-Deoxy-9-methylene-$PGE_2$.

A mixture of 9-deoxy-9-methylene-$PGE_2$ methyl ester (75 mg.), 10 percent aqueous potassium hydroxide solution (1 ml.) and 2 ml. of methanol is stirred 90 minutes at 25° C. The mixture is then diluted with ice and water, acidified with cold 2M aqueous potassium bisulfate solution, and extracted several times with ethyl acetate. The combined extracts are washed with brine, dried with anhydrous sodium sulfate, and evaporated under reduced pressure to give 9-deoxy-9-methylene-$PGE_2$.

Example 51:
9-Deoxy-9-methylene-16,16-dimethyl-$PGE_2$ Methyl Ester.

A. 16,16-Dimethyl-$PGE_2$ (300 mg.) is transformed first to its methyl ester with excess diazomethane in a mixture of diethyl ether and methanol, and then to its 11,15-bis-(trimethylsilyl ether) by the procedure of Example 49, part A.

B. A tetrahydrofuran solution of methylmagnesium chloride (2 ml.; 2M) is added dropwise to a stirred solution ester N,S-dimethyl-S-phenyl-sulfoximine (700 mg.) in 10 ml. of tetrahydrofuran at 0° C. The mixture is stirred 20 minutes at phosphoric C. and is then cooled to −78° C. A solution of the 16,16-dimethyl-$PGE_2$ methyl about 11,15-bis-(trimethylsilyl ether) obtained in A above in 30 ml. of tetrahydrofuran is added, and the mixture is stirred at −78° C. for 1.5 hours. Then the mixture is poured into a mixture of ice, water, ammonium chloride, and diethyl ether. This mixture is extracted several times with diethyl ether, and the combined extracts are washed with brine, dried with anhydrous sodium sulfate, and evaporated under reduced pressure. The 800 mg. of residue is treated with citric acid and then with amalgamated aluminum as in Example 49, parts B and C., to give 550 mg. of residue. This is chromatographed on 100 g. of neutral silica, packing with ethyl acetate-hexane (2:8 by volume) and eluting with ethyl acetate-hexane (1:1 by volume), collecting 10-ml. fractions. Fractions 66–99 are combined and evaporated under reduced pressure to give 69 mg. of 9-deoxy-9-methylene-16,16-dimethyl-$PGE_2$ methyl ester; infrared absorption of 3500, 3000, 1750, 1670, 1440, 1080, 975 and 890 cm$^{-1}$; NMR peaks at 5.70–5.2 (multiplet), 5.05–4.75 (broad singlet), 3.65 (singlet), 3.95–3.55 (multiplet), 3.05 (singlet, shifts downfield on cooling) and 0.85 and 0.80 (singlets) δ.

Exmaple 52:
9-Deoxy-9-methylene-16,16-dimethyl-$PGE_2$.

Aqueous sodium hydroxide solution (2.5 ml.; 3N) is added gradually during 2.5 minutes to a solution of 9-deoxy-9-methylene-16,16-dimethyl-$PGE_2$ methyl ester in 5 ml. of methanol under nitrogen and at about 0° C. The mixture is allowed to warm to about 25° C. and is maintained at 25° C. for a total of about 2 hours. Then, the mixture is diluted with 100 ml. of water, washed twice with diethyl ether, acidified with aqueous 1N sodium bisulfate solution with cooling, and extracted three times with ethyl acetate. The combined extracts are washed with brine, dried with anhydrous sodium sulfate, and evaporated under reduced pressure. The residue (80 mg.) is chromatographed on 10 g. of silica (Mallinckrodt CC-4), packing with ethyl acetate-hexane (4:6 by volume) and eluting with ethyl acetate-hexane (8:2 by volume), collecting 2-ml. fractions. Fractions 19–24 are combined and evaporated under reduced pressure to give 63 mg. of 9-deoxy-9-methylene-16,16-dimethyl-$PGE_2$; mass spectrum of trimethylsilyl derivative: M$^+$(found)=594; peaks also at m/e 579.3706 (M-$CH_3$) (theory for $C_{31}H_{59}Si_3O_4$=579.3721), 504, 495, 489, 405, and 243.

Example 53: 9-Deoxy-9-methylene-$PGE_1$ and its Methyl Ester.

Following the procedures of Examples 49 and 51, $PGE_1$ methyl ester is transformed to 9-deoxy-9-methylene-$PGE_1$ methyl ester. Then, following the procedures of Examples 50 and 52, the latter methyl ester is transformed to 9-deoxy-9-methylene-$PGE_1$.

Example 54: 9-Deoxy-9-methylene-15β-$PGE_1$ and its Methyl Ester.

Following the procedures of Examples 49 and 51, 15β-$PGE_1$ methyl ester is transformed to 9-deoxy-9-methylene-15β-$PGE_1$ methyl ester. Then, following the procedures of Examples 50 and 52, the latter methyl ester is transformed to 9-deoxy-9-methylene-15β-$PGE_1$.

Example 55: 9-Deoxy-9-methylene-15β-PGE$_2$ and its Methyl Ester.

Following the procedures of Examples 49 and 51, 15β-PGE$_2$ methyl ester is transformed to 9-deoxy-9-methylene-15β-PGE$_2$ methyl ester. Then, following the procedures of Examples 50 and 52, the latter methyl ester is transformed to 9-deoxy-9-methylene-15β-PGE$_2$.

Also following the procedures of Examples 49 and 51, the methyl ester of each of 15α-methyl-PGE$_1$, 15α-methyl-PGE$_2$, 15α-ethyl-PGE$_2$, 15β-methyl-PGE$_1$, 15β-methyl-PGE$_2$, 15β-16,16-dimethyl-PGE$^1$, 15β-16,16-dimethyl-PGE$_2$, 16-methyl-PGE$_1$, 16-methyl-PGE$_2$, and 15β-16-methyl-PGE$_2$ are transformed to the methyl ester of 9-deoxy-9-methylene-15α-methyl-PGE$_1$, 9-deoxy-9-methylene-15α-methyl-PGE$_2$, 9-deoxy-9-methylene-15α-ethyl-PGE$_2$, 9-deoxy-9-methylene-15β-methyl-PGE$_1$, 9-deoxy-9-methylene-15β-methyl-PGE$_2$, 9-deoxy-9-methylene-15β-16,16-dimethyl-PGE$_1$, 9-deoxy-9-methylene-15β-16,16-dimethyl-PGE$_2$, 9-deoxy-9-methylene-16-methyl-PGE$_1$, 9-deoxy-9-methylene-16-methyl-PGE$_2$, and 9-deoxy-9-methylene-15β-16-methyl-PGE$_2$, respectively. Then, following the procedures of Examples 50 and 52, each of those methyl esters is transformed to the corresponding free acid.

Further following the procedures of Examples 49 and 51, the ethyl, propyl, isopropyl, butyl, isobutyl, sec.-butyl, and tert.-butyl esters of PGE$_2$ are each transformed to the corresponding ester of 9-deoxy-9-methylene-PGE$_2$. Also following the procedure of Example 49, the alkyl esters of 2, 3, and 4 carbon atoms in the alkyl moiety of PGE$_1$, 16,16-dimethyl-PGE$_2$, and 15α-methyl-PGE$_2$ are each transformed to the corresponding esters of the corresponding 9-deoxy-9-methylene-PGE-type compound. Further, also following the procedure of Example 49, the alkyl esters of 2, 3, and 4 carbon atoms in the alkyl moiety of each of the other PGE$_1$-type and PGE$_2$-type compounds metnioned above and each transformed to the corresponding ester of the corresponding 9-deoxy-9-methylene-PGE-type compound.

Example 56:
9,11-Dideoxy-11α,9α-epoxymethano-PGF$_2$ α
(Formula XXIII; R$_1$, R$_2$, R$_3$=H;

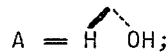

Z=cis-CH=CH—).

A. Triphenylchlorosilane (11.1 g.) is added in one portion with stirring to a solution of 9-deoxy-9-methylene-PGE$_2$ methyl ester (6.5 g.) in 65 ml. of pyridine at 0° C. under nitrogen. The mixture is allowed to warm to about 25° C. and is stirred at 25° C. under nitrogen for 2 hours. Then, an additional 11.1 g. of triphenylchlorosilane is added, and this mixture is stirred at 25° C. under nitrogen for about 65 hours. Then the mixture is poured into a mixture of water, ice, and hexane. This mixture is extracted several times with hexane, and the combined extracts are washed successively three times with water, with ice-cold aqueous potassium bisulfate solution until washes are acidic, with water, with aqueous sodium bicarbonate solution, and finally with brine, dried with anhydrous sodium sulfate, and evaporated under reduced pressure. The residue (20 g.) is chromatographed on 1.5 kg. of neutral silica, packing with ethyl acetate-hexane (3.97 by volume) and eluting successively with 10 l. ethyl acetate-hexane (5:95 by volume), 8 l. ethyl acetate-hexane (1:9 by volume), 3 l. of a gradient of ethyl acetate-hexane starting with 1:9 by volume and ending with pure ethyl acetate, and 2 l. ethyl acetate, collecting 250-ml. fractions. All fractions shown to be homogenous by tlc are combined and evaporated to give 15.3 g. of 9-deoxy-9-methylene-PGE$_2$ methyl ester 11,15-bis-(triphenylsilyl ether); homogenous by tlc.

B. A 0.5M solution of 9-borabicyclo[3.3.1]nonane in tetrahydrofuran (102 ml.) is added with stirring during 45 minutes to a solution of 9-deoxy-9-methylene-PGE$_2$ methyl ester 11,15-bis-(triphenylsilyl ether) (15.0 g.) in 600 ml. of tetrahydrofuran under nitrogen at about 0° C., and stirring is then continued for 4 hours at 0° C. To this mixture is then added successively 15 ml. of 30 percent aqueous hydrogen peroxide dropwise and then 20 ml. of 3N aqueous sodium hydroxide solution. This mixture is stirred 6 hours at 0° C, and then diluted with brine and extracted several times with ethyl acetate. The combined extracts are washed three times with brine, dried with anhydrous sdoium sulfate, and evaporated under reduced pressure. The resulting residue (36 g.) is dissolved in 600 ml. of tetrahydrofuran. To this solution at 0° C. is added 10 ml of 30 percent aqueous hydrogen peroxide and 10 ml. of 3N aqueous potassium hydroxide solution, and the mixture stirred 3 hours at 25° C. The mixture is then diluted with brine and extracted several times with ethyl acetate. The combined extracts are washed three times with brine, dried with anhydrous sodium sulfate, and evaporated under reduced pressure. The resulting residue (35.3 g.) is chromatographed on 1.5 kg. neutral silica, packing with ethyl acetate-hexane (5:95 by volume) and eluting successively wtih 10 l. ethyl acetate-hexane (1:9 by volume) and 10 l. ethyl acetate-hexane (3:7 by volume), collecting 650-ml. fractions. Fractions which are homogenous by tlc are combined and evaporated to give 10.2 g. of 9-deoxy-9α-hydroxymethyl-PGF$_2$ α methyl ester 11,15-bis-(triphenylsilyl ether).

In this procedure, the second treatment with hydrogen peroxide and potassium hydroxide is not necessary if the first such treatment is carried out at about 25° C. rather than at 0° C. as specified above.

C. Triethylamine (0.22 ml.) is added in one portion to a solution of 9-deoxy-9α-hydroxymethyl-PGF$_2$ α methyl ester 11,15-bis-(triphenylsilyl ether (0.90 g.)) in 6 ml. of dichloromethane at 0° C. under nitrogen. Then, methanesulfonyl chloride (0.1 ml.) is added dropwise during about one minute, and the mixture is stirred under nitrogen at 0° C. for 15 minutes. The resulting mixture is poured into a mixture of ice, water, sodium bicarbonate, and hexane, and this mixture is extracted several times with hexane. The combined extracts are washed successively with ice water, dilute aqueous potassium bisulfate solution, aqueous sodium bicarbonate solution, and brine, dried with anhydrous sodium sulfate, and evaporated under reduced pressure to give 1.02 g. of 9-deoxy-9α-mesyloxymethyl-PGF$_2$ α methyl ester 11,15-bis-(triphenylsilyl ether).

D. Water (30 ml.) is added to a solution of 9-deoxy-9α-mesyloxymethyl-PGF$_2$ α methyl ster 11,15-bis-(triphenylsilyl ether) (1.00 g.) in 40 ml. of tetrahydrofuran. To the resulting slurry is added one ml. of 85 percent phoshoric acid, and the mixture is heated with stirring at 40°C. for 4 hours. The mixture is allowed to stand bout 15 hours at 25° C., and is then poured into a mixture of ice and aqueous sodium bicarbonate solution. This mixture is extracted several times with ethyl acetate. The combined extracts are washed with brine, dried with anhydrous sodium sulfate, and evaporated under reduced pressure to give 1.09 of 9-deoxy-9-mesyloxymethyl-PGF$_2$ $_\alpha$ methyl ester.

E. Aqueous sodium hydroxide solution (2 ml.; 3M) is added with stirring to a solution of 9-deoxy-9-mesyloxymethyl-PGF$_2$ $_\alpha$ methyl ester (95 mg.) in 10 ml. of methanol at 0° C. The mixture is stirred 1.5 hours at 0° C. Then, another 2 ml. of 3M aqueous sodium hydroxide is added, and this mixture stirred 2 hours at about 25° C. The resulting mixture is poured into a mixture of brine, ice, and aqueous potassium bisulfate solution. This mixture is extracted several times with ethyl acetate. The combined extracts are washed with brine, dried with anhydrous sodium sulfate, and evaporated under reduced pressure. The esidue (76 mg.) is chromatographed on 10 g. of silica (Mallinckrodt CC-4), packing with ethyl acetate-hexane (2:8 by volume) and eluting with ethyl acetate-hexane (1:1 by volume), collecting 3-ml. fractions. Fractions 16–30 are combined and evaporated under reduced pressure to give 63 mg. of 9,11-dideoxy- 11$\alpha$,9$\alpha$-epoxymethano-PGF$_2$ $_\alpha$; infrared absorption at 3360, 2640, 2960, 2920, 2860, 1730, 1705, 1455, 1405, 1295, 1235, 1035, 965, 950, 940 and 875 cm$^{-1}$; NMR peaks at 6.1 (singlet; shifts downfield on cooling) 5.6–5.2 (multiplet), 4.2–3.4 (multiplet) and 0.88 (triplet)$\delta$; mass spectrum of TMS derivative: M$^+$ 494.3244 (theory for C$_{27}$H$_{50}$Si$_2$O$_4$ 494.3248), also peaks at m/e 479, 423, 404, 394, 389, 199, 173.

Example 57:
9,11-Dideoxy-11$\alpha$,9$\alpha$-epoxymethano-PGF$_2$ $_\alpha$ Methyl Ester.

Following the procedures of Example 56, parts A, B, C, and D, and then using the procedure of Example 37 rather than the procedure of Example 56, part E, 9-deoxy-9-methylene-PGE$_2$ methyl ester is transformed to 9,11-dideoxy-11$\alpha$,9$\alpha$-epoxymethano-PGF$_2$ $_\alpha$ methyl ester.

Example 58:
9,11-Dideoxy-11$\alpha$,9$\alpha$-epoxymethano-PGF$_1$ $_\alpha$ and its Methyl Ester.

Following the procedures of Examples 56 and 57, 9-deoxy-9-methylene-PGE$_1$ methyl ester is transformed through 9-deoxy-9$\alpha$-hydroxymethyl-PGF$_1$ $_\alpha$ methyl ester 11,15-bis-(triphenylsilyl ether) to 9,11-dideoxy-11$\alpha$,9$\alpha$-epoxymethano-PGF$_1$ $_\alpha$ and to its methyl ester.

Example 59:
9,11-Dideoxy-11$\alpha$,9$\alpha$-epoxymethano-15$\beta$-PGF$_1$ $_\alpha$ and its Methyl Ester.

Following the procedures of Examples 56 and 57, 9-deoxy-9-methylene-15$\beta$-PGE$_1$ methyl ester is transformed through 9-deoxy-9$\alpha$-hydroxymethyl-15$\beta$-PGF$_1$ $_\alpha$ methyl ester 11,15-bis-(triphenylsilyl ether) to 9,11-dideoxy-11$\alpha$,9$\alpha$-epoxymethano-15$\beta$-PGF$_1$ $_\alpha$ and to its methyl ester.

Example 60:
9,11-Dideoxy-11$\alpha$,9$\alpha$-epoxymethano-15$\beta$-PGF$_2$ $_\alpha$ and its Methyl Ester.

Following the procedures of Examples 56 and 57, 9-deoxy-9-methylene-15$\beta$-PGE$_2$ methyl ester is transformed through 9-deoxy-9$\alpha$-hydroxymethyl-15$\beta$-PGF$_2$ $_\alpha$ methyl ester 11,15-bis-(triphenylsilyl ether) to 9,11-dideoxy-11$\alpha$,9$\alpha$-epoxymethano-15$\beta$-PGF$_2$ $_\alpha$ and to its methyl ester.

Example 61:
9,11-Dideoxy-11$\alpha$,9$\alpha$-epoxymethano-16,16-dimethyl-PGF$_2$ $_\alpha$ and its Methyl Ester.

Following the procedures of Examples 56 and 57, 9-deoxy-9-methylene-16,16-dimethyl-PGE$_2$ methyl ester is transformed through 9-deoxy-9$\alpha$-hydroxymethyl-16,16-dimethyl-PGF$_2$ $_\alpha$ methyl ester 11,15-bis-(triphenylsilyl ether) to 9,11-dideoxy-11$\alpha$,9$\alpha$-epoxymethano-16,16-dimethyl-PGF$_2$ $_\alpha$ and to its methyl ester.

Also following the procedures of Examples 56 and 57, the methyl ester of each of 9-deoxy-9-methylene-15$\alpha$-methyl-PGE$_1$, 9-deoxy-9-methylene-15$\alpha$-methyl-PGE$_2$, 9-deoxy-9-methylene-15$\alpha$-ethyl-PGE$_2$, 9-deoxy-9-methylene-15$\beta$-methyl-PGE$_1$, 9-deoxy-9-methylene-15$\beta$-methyl-PGE$_2$, 9-deoxy-9-methylene-15$\beta$-16,16-dimethyl-PGE$_1$, 9-deoxy-9-methylene-15$\beta$-16,16-dimethyl-PGE$_2$, 9-deoxy-9-methylene-16-methyl-PGE$_1$, 9-deoxy-9-methylene-16-methyl-PGE$_2$, and 9-deoxy-9-methylene-15$\beta$-16-methyl-PGE$_2$ is transformed through the 11,15-bis-(triphenylsilyl ethers) of the corresponding 9$\alpha$-hydroxymethyl compound to 9,11-dideoxy-11$\alpha$,9$\alpha$-epoxymethano-15$\alpha$-methyl-PGF$_1$ $_\alpha$, 9,11-dideoxy-11$\alpha$,9$\alpha$-epoxymethano-15$\alpha$-methyl-PGF$_2$ $_\alpha$, 9,11-dideoxy-11$\alpha$,9$\alpha$-epoxymethano-15$\alpha$-ethyl-PGF$_2$ $_\alpha$, 9,11-dideoxy-11$\alpha$,9$\alpha$-epoxymethano-15$\beta$-methyl-PGF$_1$ $_\alpha$, 9,11-dideoxy-11$\alpha$,9$\alpha$-epoxymethano-15$\beta$-methyl-PGF$_2$ $_\alpha$, 9,11-dideoxy-11$\alpha$,9$\alpha$-epoxymethano- 15$\beta$-16,16-dimethyl-PGF$_1$ $_\alpha$, 9,11-dideoxy-11$\alpha$,9$\alpha$-epoxymethano-15$\beta$-16,16-dimethyl-PGF$_2$ $_\alpha$, 9,11-dideoxy-11$\alpha$,9$\alpha$-epoxymethano-16-methyl-PGF$_1$ $_\alpha$, 9,11-dideoxy-11$\alpha$,9$\alpha$-epoxymethano-16 -methyl-PGF$_2$ $_\alpha$, and 9,11-dideoxy-1$\alpha$,-9$\alpha$-epoxymethano-15$\beta$-16-methyl-PGF$_2$ $_\alpha$ and the methyl ester of each of those, respectively.

Further, following the procedure of Example 56, the ethyl, propyl, isopropyl, butyl, isobutyl, sec.-butyl, and t-butyl esters of 9-deoxy-9-methylene-PGE$_2$ are each transformed through the corresponding ester of 9-deoxy-9$\alpha$-hydroxymethyl-PGF$_2$ $_\alpha$ 11,15-bis-(triphenylsilyl ether) to the corresponding ester of 9,11-dideoxy-11$\alpha$,9$\alpha$-epoxymethanol-PGF$_2$ $\alpha$. Also following the procedure of Example 56, the alkyl esters of 2, 3, and 4 carbon atoms in the alkyl moiety of 9-deoxy-9-methylene-PGE$_1$, 9-deoxy-9-methylene-16,16-dimethyl-PGE$_2$, and 9-deoxy-9-methylene-15$\alpha$-methyl-PGE$_2$ are each transformed through the corresponding ester of 9-deoxy-9$\alpha$-hydroxymethyl-PGF$_1$ $_\alpha$ 11,15-bis-(triphenylsilyl ether), 9-deoxy-9$\alpha$-hydroxymethyl-16,16-dimethyl-PGF$_2$ $\alpha$ 11,15-bis-(triphenylsilyl ether), and 9-deoxy-9$\alpha$-hydroxymethyl-15$\alpha$-methyl-PGF$_2$ $_\alpha$ 11,15-bis-(triphenylsilyl ether) respectively, to the corresponding ester of 9,11 dideoxy-11$\alpha$,9$\alpha$-epoxymethano-PGF$_1$ $_\alpha$, 9,11-dideoxy-11$\alpha$,9$\alpha$-epoxymethano-16,16-dimethyl-PGF$_2$ $_\alpha$, and 9,11-dideoxy-11$\alpha$,9$\alpha$-epoxymethano-15$\alpha$-methyl-PGF$_2$ $_\alpha$. Further, also following the procedure of Example 56, the alkyl esters of 2, 3, and 4 carbon atoms in the alkyl moiety of each of the 9-deoxy-9-methylene-PGE-type compounds mentioned above is transformed through the corresponding ester of the corresponding 11,15-bis-(triphenylsilyl ether) of the 9-deoxy-9$\alpha$-hydroxymethyl-PGF $\alpha$ -type compound to the corresponding ester of the corresponding 9,11-dideoxy-11$\alpha$,9$\alpha$-epoxymethano-PGFtype compound.

Example 62: 9-Deoxy-9α-hydroxymethyl-PGF$_{2\alpha}$ Methyl Ester.

A mixture of 9-deoxy-9α-hydroxymethyl-PGF$_{2\alpha}$ methyl ester 11,15-bis-(triphenylsilyl ether) (1.00 g.), tetrahydrofuran (40 ml.), water (30 ml.), and 85 percent phosphoric acid (1 ml.) is stirred under nitrogen at about 25° C. for 18 hours. The resulting clear solution is partially evaporated under reduced pressure to remove the tetrahydrofuran, and the residue is diluted with brine and then extracted several times with ethyl acetate. The combined extracts are washed successively with aqueous sodium bicarbonate solution and brine, dried with anhydrous magnesium sulfate, and evaporated under reduced pressure. The residue is chromatographed on 60 g. of neutral silica, packing with ethyl acetate and eluting successively with 1.3 l. of ethyl acetate and 500 ml. of methanol-ethyl acetate (2:8 by volume), collecting 8-ml. fractions. Fractions 124–175 are combined and evaporated under reduced pressure to give 365 mg. of 9-deoxy-9α-hydroxymethyl-PGF$_{2\alpha}$ methyl ester; infrared absorption at 3450, 3000, 1750, 1675, 1440, 1025 and 970 cm$^{-1}$; NMR peaks at 5.6–5.2 (multiplet), 4.2–3.5 (multiplet), and 3.65 (singlet) δ.

Example 63: 9-Deoxy-9α-hydroxymethyl-PGF$_{2\alpha}$.

Following the procedures of Examples 50 and 52, 9-deoxy-9α-hydroxymethyl-PGF$_{2\alpha}$ methyl ester is transformed to 9-deoxy-9α-hydroxymethyl-PGF$_{2\alpha}$.

Example 64: 9-Deoxy-9α-hydroxymethyl-PGF$_{1\alpha}$ and its Methyl Ester.

Following the procedures of Examples 62 and 63, 9-deoxy-9α-hydroxymethyl-PGF$_{1\alpha}$ methyl ester 11,15-bis-(triphenylsilyl ether) is transformed to 9-deoxy-9α-hydroxymethyl-PGF$_{1\alpha}$ methyl ester, and then to the free acid form of that.

Example 65: 9-Deoxy-9α-hydroxmethyl-15β-PGF$_{1\alpha}$ and its Methyl Ester.

Following the procedures of Examples 62 and 63, 9-deoxy-9α-hydroxymethyl-15β-PFG$_{1\alpha}$ methyl ester 11,15-bis-(triphenylsilyl ether) is transformed to 9-deoxy-9α-hydroxymethyl-15β-PGF$_{1\alpha}$ methyl ester, and then to the free acid form of that.

Example 66: 9-Deoxy-9α-hydroxymethyl-15β-PGF$_{2\alpha}$ and its Methyl Ester.

Following the procedures of Examples 62 and 63, 9-deoxy-9α-hydroxymethyl-15β-PGF$_{2\alpha}$ methyl ester 11,15-bis-(triphenylsilyl ether) is transformed to 9-deoxy-9α -hydroxymethyl-15β-PGF$_{2\alpha}$ methyl ester, and then to the free acid form of that.

Example 67: 9-Deoxy-9α-hydroxymethyl-16,16-dimethyl-PGF$_{2\alpha}$ and its Methyl Ester.

Following the procedures of Examples 62 and 63, 9-deoxy-9αhydroxymethyl-16,16-dimethyl-PGF$_{2\alpha}$ methyl ester 11,15-bis-(triphenylsilyl ether) is transformed to 9-deoxy-9α-hydroxymethyl-16,16-dimethyl-PGF$_{2\alpha}$ methyl ester, and then to the free acid form of that.

Also following the procedures of Examples 62 and 63, the methyl ester 11,15-bis-(triphenylsilyl ether) of each of 9-deoxy-9α-hydroxymethyl-15α-methyl-PGF$_{1\alpha}$, 9-deoxy-9α-hydroxymethyl-15α-methyl-PGF$_{2\alpha}$, 9-deoxy-9α-hydroxymethyl-15α-ethyl-PGF$_{2\alpha}$, 9-deoxy-9α-hydroxymethyl-15β-methyl-PGF$_{1\alpha}$, 9-deoxy-9α-hydroxymethyl-15β-methyl-PGF$_{2\alpha}$, 9-deoxy-9α-hydroxymethyl-15β-16,16-dimethyl-PGF$_{1\alpha}$, 9-deoxy-9α-hydroxymethyl-15β-16,16-dimethyl-PGF$_{2\alpha}$, 9-deoxy-9α-hydroxymethyl-16-methyl-PGF$_{1\alpha}$, 9-deoxy-9α-hydroxymethyl-16-methyl-PGF$_{2\alpha}$, and 9-deoxy-9α-hydroxymethyl-15β-16-methyl-PGF$_{2\alpha}$ is transformed to the corresponding 9α-hydroxymethyl methyl ester, and then to the free acid form of each of those.

Further, following the procedure of Example 62, the ethyl, propyl, isopropyl, butyl, isobutyl, sec.-butyl, and t-butyl esters of 9-deoxy-9α-hydroxymethyl-PGF$_{2\alpha}$ 11,15-bis-(triphenylsilyl ether) are each transformed to the corresponding ester of 9-deoxy-9α-hydroxymethyl-PGF$_{2\alpha}$. Also following the procedure of Example 62, the alkyl esters of 2,3, and 4 carbon atoms in the alkyl moiety of the 11,15-bis-(triphenylsilyl ether) of 9-deoxy-9α-hydroxymethyl-PGF$_{1\alpha}$, 9-deoxy-9α-hydroxvmethyl-16,16-dimethyl-PGF$_{2\alpha}$, and 9-deoxy-9α-hydroxymethyl-15α-methyl-PGF$_{2\alpha}$ are each transformed to the corresponding esters of 9-deoxy-9α-hydroxy-methyl-PGF$_{1\alpha}$, 9-deoxy-9α-hydroxymethyl-16,16-dimethyl-PGF$_{2\alpha}$, and 9-deoxy-9α-hydroxymethyl-15α-methyl-PGF$_{2\alpha}$, respectively. Further, also following the procedure of Example 62, the alkyl esters of 2, 3, and 4 carbon atoms in the alkyl moiety of each of the 11,15-bis-(triphenylsilyl ethers) of each of the other 9-deoxy-9α-hydroxymethyl-PGF$_\alpha$ -type compounds mentioned above is transformed to the corresponding ester of the corresponding 9-deoxy-9α-hydroxymethyl-PGF$_\alpha$ -type compound.

Example 68: 9,11-Dideoxy-9α,11α-epoxymethano-PGF$_{2\alpha}$ Methyl Ester 15-Acetate.

A. A solution of excess diazomethane in diethyl ether at 0° C. is added to a solution of 9,11-dideoxy-9α,11α-epoxymethano-PGF$_{2\alpha}$ (638 mg.) in diethyl ether at 0° C. After 5 minutes at 0° C., the mixture is evaporated with a stream of nitrogen. The residue is chromatographed on 70 g. of neutral silica, packing with ethyl acetate-hexane (1:9 by volume) and eluting with ethyl acetate-hexane (35:65 by volume), collecting 7-ml. fractions. Fractions 97–140 are combined and evaporated under reduced pressure to give 570 mg. of 9,11-dideoxy-9α,11α-epoxymethano-PGF$_{2\alpha}$ methyl ester; NMR peaks at 7.3 (singlet), 5.65–5.15 (multiplet), 4.2–3.85 (multiplet), 3.65 (singlet), and 3.85–3.25 (six line pattern) δ.

B. 9,11-Dideoxy-9α,11α-epoxymethano-PGF$_{2\alpha}$ methyl ester (200 mg.) is dissolved in a mixture of 4 ml. of pyridine and 1 ml. of acetic anhydride, and the resulting solution is stirred 18 hours at 25° C. The mixture is then poured into a mixture of ice, brine, diethyl ether, and 25 ml. of 2N aqueous potassium bisulfate solution, and this mixture is extracted several times with diethyl ether. The combined extracts are washed successively with cold 1N aqueous potassium bisulfate solution, water, aqueous sodium bicarbonate solution, and brine, dried with anhydrous sodium sulfate, and evaporated under reduced pressure to give 235 mg. of a yellow oil. This oil is chromatographed on 18 g. of neutral silica, packing with ethyl acetate-hexane (5:95 by volume) and eluted with ethyl acetate-hexane (3:10 by volume), collecting 3-ml. fractions. Fractions 21–34 are combined and evaporated under reduced pressure to give 200 mg. of 9,11-dideoxy-9α,11α-epoxymethano-PGF$_{2\alpha}$ methyl ester 15-acetate; infrared absorption at 1745, 1365, 1240, 1155, 1045, 1020, 970, and 875 cm$^{-1}$; NMR peaks at 5.65–5.05 (multiplet), 4.12 (singlet), 3.65 (singlet), 3.85–3.35 (six-line pattern), and 2.01 (singlet)δ. This compound is also prepared by the procedure of Example 43.

Example 69: 9α,11α-(Epoxymethano)prostanoic Acid (Formula XXV: X is —O—, Y is a valence bond, and R$_1$ is hydrogen).

Palladium catalyst (40 mg., 10 percent on carbon) is added to a solution containg 9,11-dideoxy-9α,11α-epoxymethano-PGF$_{2\alpha}$ methyl ester 15-acetate (180 mg.) in 18 ml. of ethanol containing 0.18 ml. of aqueous concentrated hydrochloric acid. The resulting mixture is shaken in a hydrogen atmosphere at atmospheric pressure and about 25° C. until uptake of hydrogen ceases (about 45 minutes). The mixture is then filtered through a pad of Celite in a carbon dioxide atmosphere, and the filter pad is washed with three 5-ml. portions of ethanol. Aqueous potassium hydroxide solution (5 ml. of 3N) is added to the combined filtrate and washings, and the mixture is allowed to stand 2 hours at 25° C. The ethanol is then removed under reduced pressure, and the aqueous residue is successively diluted with water, acidified with aqueous potassium bisulfate solution, and extracted several times with ethyl acetate. The combined extracts are washed with brine, dried with anhydrous sodium sulfate, and evaporated under reduced pressure. The residue (190 mg.) is chromatographed on 20 g. of acid-washed silica (Mallinckrodt CC-4), packing with ethyl acetate-hexane (5:95 by volume) and eluted successively with 50 ml. ethyl acetate-hexane (5:95 by volume), 90 ml. ethyl acetate-hexane (10:90 by volume), 100 ml. ethyl acetate-hexane (15:85 by volume), and 200 ml. ethyl acetate-hexane (2:8 by volume), collecting 5-ml. fractions. Fractions 46–65 are combined and evaporated under reduced pressure to give 80 mg. of 9α,11α-(epoxymethano)prostanoic acid; infrared absorption at 3000, 2670 (sh), 2920, 2850, 1710, 1460, 1415, 1380, 1290, 1255, 1235, 1215, 1195, 1060, 1030, 965, 930, 865, and 725 cm$^{-1}$; NMR peaks at 4.15 (singlet) and 3.80–3.35 (six-line pattern) δ.

Example 70: 9α,11α-(Epoxymethano)prostanoic Acid Methyl Ester.

9,11-Dideoxy-9α,11α-epoxymethano-PGF$_{2\alpha}$ methyl ester 15-acetate is subjected to the palladium and hydrochloric acid catalyzed hydrogenation and hydrogenolysis described in Example 69, but the combined filtrate and washings, instead of being treated with potassium hydroxide, are neutralized by the cautious addition of cold aqueous sodium bicarbonate solution. Following removal of most of the ethanol at reduced pressure (30° maximum temperature), the residue is extracted thoroughly with ethyl acetate. The combined extracts are washed with brine, dried with anhydrous magnesium sulfate and concentrated at reduced pressure to give 9α,11α-(epoxymethano)prostanoic acid methyl ester.

This methyl ester has substantially the same physical properties as the methyl ester obtained by reaction of 9α,11α-(epoxymethano)prostanoic acid with diazomethane according to the procedure of Example 68.

Example 71: 9α,11α-(Epoxymethano)prostanoic Acid.

Following the procedure of Example 68, 9,11-dideoxy-9α,11α-epoxymethano-15β-PGF$_{2\alpha}$ is transformed to the corresponding methyl ester 15-acetate. This is also prepared by the procedure of Example 45. Then, following the procedure of Example 69, this methyl ester 15-acetate is transferred to 9α,11α-(epoxymethano)prostanoic acid; substantially the same physical properties as the product of Example 69.

Example 72: 9α,11α-)Epoxymethano)prostanoic Acid.

Following the procedure of Example 68, 9,11-dideoxy-9α,11α-epoxymethano-PGF$_{1\alpha}$ is transformed to the corresponding methyl ester 15-acetate. Then, following the procedure of Example 69, this methyl ester 15-acetate is transformed to 9α,11α-(epoxymethano)prostanoic acid; substantially the same physical properties as the product of Example 69.

Example 73: 9α,11α-(Epoxymethano)prostanoic Acid Methyl Ester.

Following the procedure of Example 70, 9,11-dideoxy-9α,11α-epoxymethano-15β-PGF$_{2\alpha}$ methyl ester 15-acetate is transformed to 9α,11α-(epoxymethano)prostanoic acid methyl ester; substantially the same physical properties as the product of Example 70.

Also following the procedures of Examples 69 and 70, the ethyl, propyl, isopropyl, butyl, sec.-butyl, and t-butyl esters of 9,11-dideoxy-9α,11α-epoxymethano-PGF$_{2\alpha}$ 15-acetate and of 9α,11α-epoxymethano-15β-PGF$_{2\alpha}$ 15-acetate are transformed to 9α,11α-(epoxymethano)prostanoic acid and to the corresponding alkyl esters of that.

Example 74:
9,11-Dideoxy-11α,9α-epoxymethano-PGF$_{2\alpha}$ Methyl Ester 15-Acetate.

Following the procedure of Example 68, 9,11-dideoxy-11α,9α-epoxymethano-PGF$_{2\alpha}$ (300 mg.) is transformed first to its methyl ester and then to its 15-acetate, chromatographing the 340 mg. of residue on neutral silica as described in Example 68.

Example 75: 11α,9α-(Epoxymethano)prostanoic Acid.

Palladium catalyst (50 mg., 10 percent on carbon) is added to a solution of 9,11-dideoxy-11α,9α-epoxymethano-PGF$_{2\alpha}$ methyl ester 15-acetate (227 mg.) in 25 ml. of ethanol containing 1 % concentrated aqueous hydrochloric acid. The resulting mixture is shaken in a hydrogen atmosphere of atmospheric pressure and about 25° C. until uptake of hydrogen ceases (6 minutes). This mixture is then filtered through a pad of Celite, and the filter pad is washed with ethanol. Aqueous sodium hydroxide solution is added to the combined filtrate and washing, and about one-half of the ethanol is removed under reduced pressure. The remaining mixture is allowed to stand 3 hours at 25° C. The remaining ethanol is the removed under reduced pressure, and the aqueous residue is acidified with cold aqueous 2N potassium bisulfate solution and extracted several times with ethyl acetate. The combined extracts are washed with brine, dried with anhydrous sodium sulfate, and evaporated under reduced pressure. The residue is chromatographed on acid-washed silica (Mallinckrodt CC-4), packing with ethyl acetate-hexane (5:95 by volume) and eluting with ethyl acetate-hexane (15:85 by volume), collecting 5-ml. fractions.

Fractions 18–38 are combined and evaporated under reduced pressure to give 157 mg. of 11α,9α-(epoxymethano)prostanoic acid; infrared absorption 3000, 2680, 2920, 2860, 1735, 1710, 1460, 1415, 1290, 1240, 1165, 1120, 1060, 1025, 955, 935, 885 and 870 cm$^{-1}$; NMR peaks at 9.18 (singlet, shifts on cooling), 4.05 (singlet), 3.9–3.4 (six-line pattern) δ; mass spectrum for TMS derivative: M$^+$ 410.3206 (theory for $C_{24}H_{46}SiO_3$: 410.3216) also peaks at m/e 395, 392, 380, 342, 284, 257, 209.

Example 76: 11α,9α-(Epoxymethano)prostanoic Acid Methyl Ester.

9,11-Dideoxy-11α,9α-epoxymethano-PGF$_{2\alpha}$ methyl ester 15-acetate is subjected to the palladium and hydrochloric acid catalyzed hydrogenation and hydrogenolysis described in Example 75, but the combined filtrate and washing, instead of being treated with sodium hydroxide, is processed according to the procedure of Example 70 to give 11α,9α-(epoxymethano)-prostanoic acid methyl ester. This methyl ester has substantially the same physical properties as the methyl ester obtained by reaction of 11α,9α-(epoxymethano)-prostanoic acid with diazomethane according to the procedure of Example 68.

Example 77: 11α,9α-(Epoxymethano)prostanoic Acid.

following the procedure of Example 68, 9,11-dideoxy-11α,9α-epoxymethano-PGF$_{1\alpha}$ is transformed to the corresponding methyl ester 15-acetate. Then, following the procedure of Example 75, this methyl ester 15-acetate is transformed to 11α,9α-(epoxymethano)prostanoic acid; substantially the same physical properties as the product of Example 75.

Example 78: 11α,9α-(Epoxymethano)prostanoic Acid.

Following the procedure of Example 68, 9,11-dideoxy-11α,9α-epoxymethano-15β-PGF$_{2\alpha}$ is transformed to the corresponding methyl ester 15-acetate. Then, following the procedure of Example 75, this methyl ester 15-acetate is transformed to 11α,9α-(epoxymethano)prostanoic acid; substantially the same physical properties as the product of Example 75.

Example 79: 11α,9α-(Epoxymethano)prostanoic Acid Methyl Ester.

Following the procedure of Example 76, 9,11-dideoxy-11α,9α-epoxymethano-15β-PGF$_{2\alpha}$ methyl ester 15-acetate is transformed to 11α,9α-(epoxymethano)prostanoic acid methyl ester; substantially the same physical properties as the product of Example 76.

Also following the procedures of Examples 75 and 76, the ethyl, propyl, isopropyl, butyl, isobutyl, sec.-butyl and t-butyl esters of 9,11-dideoxy-11α,9α-epoxymethano-PGF$_{2\alpha}$ 15-acetate and of 11α,9α-epoxymethano-15β-PGF$_{2\alpha}$ 15-acetate are transformed to 11α,9α-(epoxymethano)prostanoic acid and to the corresponding alkyl esters of that.

I clam:

1. A compound of the formula:

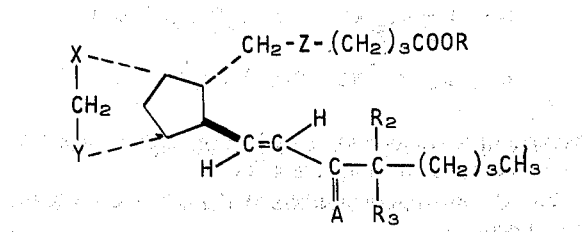

wherein X and Y are —O— or a valence bond with the proviso that one of X and Y is —O— and the other is a valence bond; wherein Z is —CH$_2$CH$_2$— or cis-CH=CH—, wherein R is hydrogen, alkyl of one to 4 carbon atoms, inclusive, or a pharmacologically acceptable cation; wherein R$_2$ and R$_3$ are hydrogen, methyl, or ethyl; and wherein A is

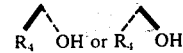

wherein R$_4$ is hydrogen, methyl, or ethyl with the proviso that R$_2$ and R$_3$ are both hydrogen, when R$_4$ is methyl or ethyl.

2. A compound of the formula:

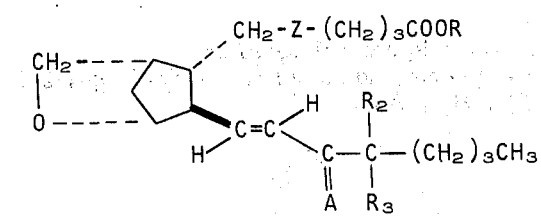

being a compound according to claim 1 wherein X is a valence bond, Y is —O—, and Z, R, R$_2$, R$_3$, and A are as defined in claim 1.

3. A compound of the formula:

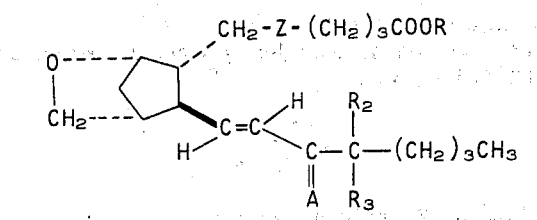

being a compound according to claim 1 wherein X is —O—, Y is a valence bond, and Z, R, R$_2$, R$_3$, and A are as defined in claim 1.

4. A compound according to claim 2 wherein Z is —CH$_2$CH$_2$—, A is

and R$_2$ and R$_3$ are both hydrogen.

5. A compound according to claim 2 wherein Z is —CH$_2$CH$_2$—, A is

and R$_2$ and R$_3$ are both methyl.

6. A compound according to claim 2 wherein Z is —CH$_2$CH$_2$—, A is

and R$_2$ and R$_3$ are both hydrogen.

7. A compound according to claim 2 wherein Z is cis-CH=CH—, A is

and R₂ and R₃ are both hydrogen.

8. A compound according to claim 2 wherein Z is cis-CH=CH—, A is

and R₂ and R₃ are both methyl.

9. A compound according to claim 2 wherein Z is cis-CH=CH—, A is

and R₂ and R₃ are both hydrogen.

10. A compound according to claim 3 wherein Z is —CH₂CH₂—, A is

and R₂ and R₃ are both hydrogen.

11. A compound according to claim 3 wherein Z is —CH₂CH₂—, A is

and R₂ and R₃ are both methyl.

12. A compound according to claim 3 wherein Z is —CH₂CH₂—, A is

and R₂ and R₃ are both hydrogen.

13. A compound according to claim 3 wherein Z is cis-CH=CH—, A is

and R₂ and R₃ are both hydrogen.

14. A compound according to claim 3 wherein Z is cis-CH=CH—, A is

and R₂ and R₃ are both methyl.

15. A compound according to claim 3 wherein Z is cis-CH=CH—, A is

and R₂ and R₃ are both hydrogen.

16. A compound of the formula:

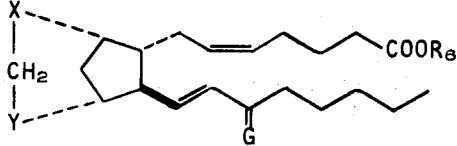

wherein X and Y are —O— or a valence bond with the proviso that one of X and Y is —O— and the other is a valence bond; wherein R₆ is alkyl of one to 4 carbon atoms, inclusive; and wherein G is

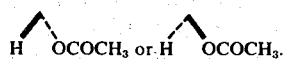

17. A compound of the formula:

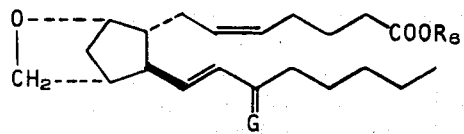

being a compound according to claim 16 wherein X is —O— and Y is a valence bond.

18. A compound according to claim 17 wherein G is

and R₆ is methyl.

19. A compound of the formula:

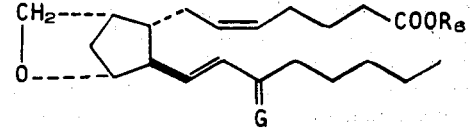

being a compound according to claim 16 wherein X is a valence bond and Y is —O—.

20. A compound according to claim 19 wherein G is

and R₆ is methyl.

21. A compound of the formula:

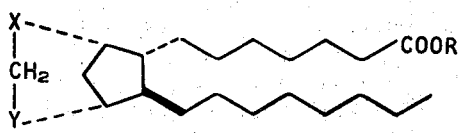

wherein X and Y are —O— or a valence bond with the proviso that one of X and Y is —O— and the other is a valence bond, and wherein R is hydrogen, alkyl of one to 4 carbon atoms, inclusive, or a pharmacologically acceptable cation.

22. A compound of the formula:

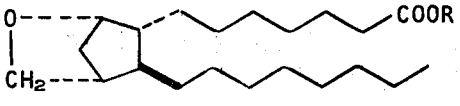

being a compound according to claim 21 wherein X is —O— and Y is a valence bond.

23. A compound according to claim 22 wherein R is hydrogen.

24. A compound of the formula:
being a compound according to claim 21 wherein X is a valence bond and Y is —O—.
25. A compound according to claim 24 wherein R is hydrogen.
* * * * *

UNITED STATES PATENT AND TRADEMARK OFFICE
CERTIFICATE OF CORRECTION

PATENT NO. : 3,950,363
DATED : April 13, 1976
INVENTOR(S) : Gordon L. Bundy

It is certified that error appears in the above-identified patent and that said Letters Patent are hereby corrected as shown below:

Column 3, lines 10-11, "prostaglandin $F_2$ ($PGF_2$ )" should read -- prostaglandin $F_{2\alpha}$ ($PGF_{2\alpha}$) --. Column 21, line 59, "1460, 1375," should read -- 1460, 1400, 1375, --. Column 22, lines 2-5, "$R_3$ = H; -hydroxymethyl-PGE A = H OH;" should read -- $R_3$ = H; A = H OH; --; line 47, "N-methyl-N-nitro-N-" should read -- N-methyl-N'-nitro-N- --. Column 23, line 47, "11-doexy-11α-hydroxymethyl-$PGE_1$," should read -- 11-deoxy-11α-hydroxymethyl-$PGE_1$, --. Column 25, lines 39-41, "A = $CH_3$ OH;" should read -- A = H OH; --. Column 28, lines 21-22, "11-deoxy-11α-hydroxymethyl-15β-$PGF_2$ methyl ester" should read -- 11-deoxy-11α-hydroxymethyl-15β-$PGF_{2\alpha}$ methyl ester --. Column 32, line 4, "ethyl acetane-hexane" should read -- ethyl acetate-hexane --. Column 34, lines 22-23, "9,11-dideoxy-9α,11α-epoxymethane-$PGF_2$-type" should read -- 9,11-dideoxy-9α,11α-epoxymethano-$PGF_2$-type --;

line 50, " A = $CH_3$ OH;" should read -- A = H OH; --. Column 35, line 68, "solution ester N,S-dimethyl-S-phenyl-sulfoximine" should read -- solution of N,S-dimethyl-S-phenyl-sulfoximine --. Column 36, line 2, "stirred 20 minutes at phosphoric C." should read -- stirred 20 minutes at $0°$ C. --; lines 3-4, "16,16-dimethyl-$PGE_2$ methyl about" should read -- 16,16-dimethyl-$PGE_2$ methyl ester --; line 38, "1N sodium bisulfate" should read -- 2N sodium bisulfate --. Column 37, lines 16-17, "9-deoxy-9-methylene-15α-methyl-$PGE_1$9-deoxy-9-methylene-15α-methyl-$PGE_2$," should read -- 9-deoxy-9-methylene-15α-methyl-$PGE_1$, 9-deoxy-9-methylene-15α-methyl-$PGE_2$, --.

UNITED STATES PATENT AND TRADEMARK OFFICE
CERTIFICATE OF CORRECTION

PATENT NO. : 3,950,363
DATED : April 13, 1976
INVENTOR(S) : Gordon L. Bundy

It is certified that error appears in the above-identified patent and that said Letters Patent are hereby corrected as shown below:

Column 38, line 2, "(3.97 by volume) should read -- (3:97 by volume); line 64, "methyl ster" should read -- methyl ester --. Column 40, line 10, "9-deoxy-9-methylene-16,16-dimethyl-$PGE_{2\alpha}$ methyl ester" should read -- 9-deoxy-9-methylene-16,16-dimethyl-$PGE_2$ methyl ester --; lines 37-38, "9,11-dideoxy-1α,9α-epoxymethano-15β-16-methyl-$PGF_{2\alpha}$" should read -- 9,11-dideoxy-11α,9α-epoxymethano-15β-16-methyl-$PGF_{2\alpha}$ --; lines 45-46, "9,11-dideoxy-11α,9α-epoxymethanol-$PGF_{2\alpha}$." should read -- 9,11-dideoxy-11α,9α-epoxymethano-$PGF_{2\alpha}$. --. Column 44, line 29, "butyl, sec.-butyl," should read -- butyl, isobutyl, sec.-butyl, --; line 59, "ethanol is the removed" should read -- ethanol is then removed --.

Signed and Sealed this

Thirteenth Day of September 1977

[SEAL]

Attest:

RUTH C. MASON
Attesting Officer

LUTRELLE F. PARKER
Acting Commissioner of Patents and Trademarks